United States Patent [19]

Inomata et al.

[11] Patent Number: 5,756,475
[45] Date of Patent: May 26, 1998

[54] ISOPRENE DERIVATIVES

[75] Inventors: Kohei Inomata; Toshihiro Takahashi; Hitoshi Inoue; Makoto Yanai; Hiroyuki Yamazaki; Masashi Suzuki; Tsutomu Takasawa; Kouji Kawamura; Norio Oshida; Hiroyuki Ikemoto; Takao Kishiye, all of Saitama-ken, Japan

[73] Assignee: Nisshin Flour Milling Co., Ltd., Tokyo, Japan

[21] Appl. No.: 791,165

[22] Filed: Jan. 30, 1997

[30] Foreign Application Priority Data

Jan. 31, 1996 [JP] Japan ................. 8-015080

[51] Int. Cl.$^6$ ............ A01N 43/04; A01N 33/02; C07C 211/00
[52] U.S. Cl. ............ 514/34; 514/655; 514/937; 514/938; 564/367; 564/370
[58] Field of Search ............ 514/34, 655, 937, 514/938; 564/367, 370

[56] References Cited

U.S. PATENT DOCUMENTS

| | | | |
|---|---|---|---|
| 4,303,588 | 12/1981 | Okabe et al. | 260/404 |
| 5,004,756 | 4/1991 | Ogawa et al. | 514/655 |
| 5,182,267 | 1/1993 | Ogawa et al. | 514/34 |

FOREIGN PATENT DOCUMENTS

| | | |
|---|---|---|
| 0 355 604 | 2/1990 | European Pat. Off. |
| 355604 | 2/1990 | European Pat. Off. |
| 0 623 621 | 11/1994 | European Pat. Off. |
| 2 505 826 | 11/1982 | France |
| 2-138211 | 5/1990 | Japan |
| 5-16411 | 3/1993 | Japan |
| 7-10881 | 1/1995 | Japan |

OTHER PUBLICATIONS

Yamaguchi et al., "Overcoming Drug Resistance in Cancer Cells with Synthetic Isoprenoids", Journal of Nat'l Cancer Institute, vol. 76 (1986), No. 5, pp. 947–953.

Tsuruo et al., "Overcoming of Vincristine Resistance in P388 Leukemia In Vivo and In Vitro Through Enhanced Cytotoxicity of Vincristine and Vinblastine by Verapamil", Cancer Research 41, 1967–1972, May 1981.

Cardarelli et al., Differential Effects of P–Glycoprotein Inhibitors on NIH3T3 Cells Transfected with Wild–type (G185) or Mutant (V185) Multidrug Transporters.

*Primary Examiner*—John M. Ford
*Assistant Examiner*—Tamthom T. Ngo
*Attorney, Agent, or Firm*—Oblon, Spivak, McClelland, Maier & Neustadt, P.C.

[57] ABSTRACT

Isoprene derivatives of formula (I)

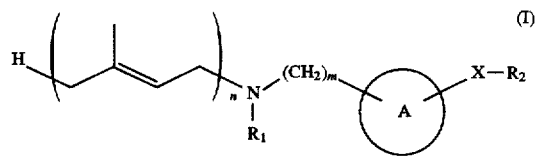

wherein m is an integer of 0 to 3, n is an integer of 5 to 12,

A is cyclo($C_3$–$C_6$)alkylene, phenylene, fluorenylene, pyrrolidinylene, piperazinylene, 9-aza-3-oxabicyclo [3.3.1]-nonylene, $R_1$ and $R_2$ are each independently benzyl, of which a phenyl ring may be substituted by 1 to 5 substituents selected from the group consisting of hydroxy, ($C_1$–$C_4$) alkyl, ($C_1$–$C_4$)alkoxy and halogen, X is a single bond or a divalent radical of —$(CH_2)_p$NH—, p is an integer of 0 to 3, or a pharmaceutically acceptable salt thereof. Those compounds are useful as multidrug resistance inhibitors for overcoming multidrug resistance of cancer and agents for enhancing an activity of anti-cancer agents.

10 Claims, No Drawings

ISOPRENE DERIVATIVES

FIELD OF THE INVENTION

This invention relates to new isoprene derivatives, processes for the preparation thereof, pharmaceutical compositions, specifically multidrug resistance inhibitors for overcoming a multidrug resistance of cancer and agents for enhancing an activity of anti-cancer agents comprising as an active ingredient said isoprene derivatives or pharmaceutically acceptable salts thereof.

BACKGROUND OF THE INVENTION

It is a common problem for human beings to overcome cancer. For the purpose, many anti-cancer agents have been developed until now, but the expression of multidrug resistance of cancer has become a clinical problem. Multidrug resistance is a phenomenon (cross-resistance) in which cancer cells resist to not only the particular anti-cancer agent administered, but also the other anti-cancer agents, due to an administration of an anti-cancer agent or a resistance of cancer cells by nature to anti-cancer agents. Reportedly, about 50% of patients newly diagnosed as cancer showed a drug resistance in the treatment of cancer, and more than 90% of the deaths showed some behaviors associated with the resistance of cancer cells to anti-cancer agents during the treatment with anti-cancer agents. Therefore, it has become extremely important in cancer chemotherapy to overcome a multidrug resistance to anti-cancer agents of cancer cells.

Although a mechanism of cancer cells causing multidrug resistance has not been clearly elucidated, it is considered to result from a reduced concentration of anti-cancer agents in the cells when said cells have acquired multidrug resistance. On the other hand, many cancer cells having multidrug resistance produce P-glycoprotein excessively and this P-glycoprotein may play a role in transporting anti-cancer agents out of the cells. P-glycoprotein is coded by a gene called MDR1 on human being. Thus the over-expression of MDR1 gene in human cancer cells is considered to be a cause of acquiring resistance (MDR1 resistance). P-glycoprotein has low substrate specificity and can bind with various kinds of compounds to transport drugs out of the cells. It follows that once P-glycoprotein expresses in cancer cells, the cells will acquire resistance to many other anti-cancer agents. In fact, it is known that many structurally different anti-cancer agents such as adriamycin, vinblastine, vincristine, actinomycin D, colchicine become a substrate for transporting outside cells by P-glycoprotein. Therefore, it is considered that inhibiting the function of P-glycoprotein will lead to overcoming multidrug resistance. It is reported that about 30% of multidrug resistance is caused by P-glycoprotein.

It is known that messenger RNA of MDR1 gene encoding P-glycoprotein expresses in normal tissue, for example, kidney, adrenal, large intestine, small intestine, intestinum colon, lung, liver, pancreas, or lymphocyte. In kidney P-glycoprotein plays a part to transport drugs out of the body. The reason why anti-cancer agents have low activity in kidney cancer where kidney cells were cancerous is that P-glycoprotein expressed in kidney will transport anti-cancer agents outside the cells. Recently, it is found that the main substance of blood brain barrier which controls transport of drugs into the brain is P-glycoprotein. This means the concentration of anti-cancer agents delivered into brain, kidney, adrenal, large intestine, small intestine, intestinum colon, lung, liver, pancreas, lymphocyte of leukemia etc., can be increased by inhibiting P-glycoprotein. Thus, P-glycoprotein inhibitors are expected to enhance effect of anti-cancer agents on brain tumor, kidney cancer, adrenal cancer, large intestine cancer, small intestine cancer, intestinum colon cancer, lung cancer, liver cancer, pancreas cancer, or leukemia etc.

In the field of cancer chemotherapy, many anti-cancer agents have been used such as mitomycin, cyclophosphamide, melphalan, nimustine, carboquone, vincristine, vinblastine, vindesine, bleomycin, 5-fluorouracil, adriamycin, cisplatin, actinomycinD, methotrexate, aclarubicin, toyomycin, neocarzinostatin, ifosfamide, etoposide, camptothecin, doxorubicin, irinotecan. Those drugs have characteristic anti-cancer spectra. Some of those anti-cancer agents are known to bring about a resistance of cancer cells to the agents by continuous or a long time administration. Further, the problem of cross-resistance has arisen. Therefore it has been required to activate or enhance the sensitivity of cancer cells having resistance to anti-cancer agents in the field of cancer chemotherapy.

Many anti-cancer agents have not only an anti-cancer activity as a main effect but also side effects such as falling-out of hair, diarrhea, nausea and vomitting. Such side effects sometimes are an obstacle to a case of cancer in the treatment with anti-cancer agents. Therefore agents for enhancing the activity of anti-cancer agents has been required for treating cancer in a small amount of dosage, with a view to reducing the side effects of anti-cancer for patients having non-resistant cancer cells as well as resistant cancer cells.

Taxol and its derivative taxotere were approved in U.S.A. in recent years, and will be done in Japan. They are expected to be one of the leading drugs of solid carcinoma chemotherapy in the future, because of having a potent and strong anti-cancer activity, particularly in the field of solid carcinoma. However, taxol is known to be a substrate for transporting outside cells by P-glycoprotein, and its activity may be weakened by MDR1 resistance. Recently, it is reported that P-glycoprotein inhibitors overcome taxol resistance in MDR1 resistance cells (Cancer Res., vol. 55, 1086–1091, 1995). This shows that P-glycoprotein inhibitors are also effective for taxol resistance.

Tsuruo et al. report that verapamil represented by the following formula (IV)

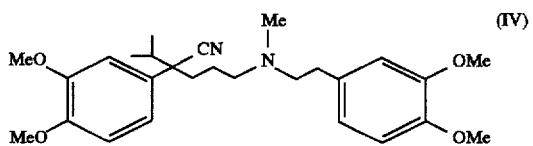

inhibits P-glycoprotein and overcomes MDR1 resistance (Cancer Res., vol. 41, 1967–1972, 1981).

Nakagawa et al., Japanese Patent Kokoku 5-16411 discloses a compound of formula (V)

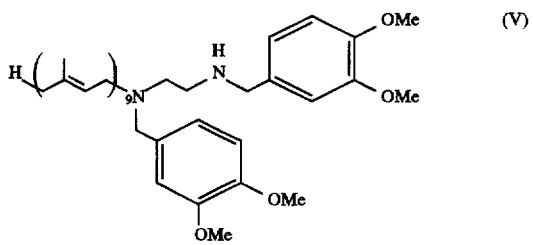

and the pharmaceutically acceptable salts thereof, which have an activity of overcoming adriamycin (ADM) resistance to ADM, one of anti-cancer drugs. Ogawa et al., Japanese Patent Kokai 2-138211 discloses that the malate of formula (V) has an activity of enhancing the anti-cancer activity.

There is no report that the compound of formula (V) enhances an anti-cancer activity of taxol in MDR1 resistance cells.

DETAILED DESCRIPTION OF THE INVENTION

We have studied many compounds for enhancing the activity of anti-cancer agents in an effort to overcome the above-mentioned problems of multidrug resistance of cancer cells. As a result, we have found that isoprene derivatives represented by formula (I) have an activity of overcoming multidrug resistance in MDR1 resistance cells, without $Ca^{2+}$ antagonist activity and with a low cytotoxicity, and also have an activity of enhancing the activity of anti-cancer agents, in particular taxol and its derivatives.

Accordingly, the present invention provides an isoprene derivative of formula (I)

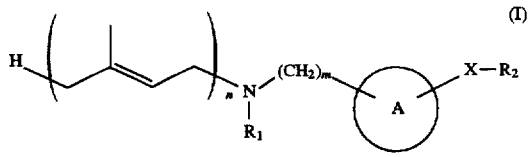

wherein m is an integer of 0 to 3, n is an integer of 5 to 12,

A is cyclo($C_3$–$C_6$)alkylene, phenylene, fluorenylene, pyrrolidinediyl, piperazinediyl, 9-aza-3-oxabicyclo [3.3.1]-nonylene, $R_1$ and $R_2$ are each independently benzyl, of which a phenyl ring may be substituted by 1 to 5 substituents selected from the group consisting of hydroxy, ($C_1$–$C_4$) -alkyl, ($C_1$–$C_4$)alkoxy and halogen, X is a single bond or a divalent radical of —($CH_2$)$_p$NH—, p is an integer of 0 to 3, and a pharmaceutically acceptable salt thereof.

The present invention also provides a pharmaceutical composition which comprises as an active ingredient a compound of formula (I), or a pharmaceutically acceptable salt thereof.

The present invention further provides a multidrug resistance inhibitor which comprises as an active ingredient a compound of formula (I) or a pharmaceutically acceptable salt thereof. Further, the present invention provides an agent for enhancing an activity of anti-cancer agents in the treatment of cancers which include brain tumor, kidney cancer, adrenal cancer, large intestine cancer, small intestine cancer, intestinum colon cancer, lung cancer, liver cancer, pancreas cancer and leukemia.

The present invention further provides an agent for enhancing the activity of taxol or its derivatives, which comprises a compound of formula (I) or a pharmaceutically acceptable salt thereof in combination with taxol and its derivatives. The taxol derivatives include, for example, taxotere.

The present invention also provides a process of preparing a compound of formula (I), which comprises reacting a compound of formula (II)

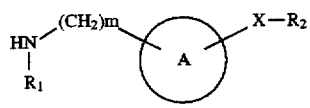

wherein m, A, X, $R_1$, and $R_2$ are as defined for formula (I) above, with a compound of formula (III)

wherein n is as defined for formula (I) above, and L is a leaving group selected from the group consisting of halogen, $C_1$–$C_4$ alkylsulfonyloxy and arylsulfonyloxy.

In the compounds of formulae (I) and (II), examples of the cyclo($C_3$–$C_6$)alkylene groups include cyclopropylene, cyclobutylene, cyclopentylene and cyclohexylene. The ($C_1$–$C_4$)alkyl group can be straight-chain or branched, examples of which include methyl, ethyl, n-propyl, isopropyl, n-butyl, sec-butyl and tert-butyl. The ($C_1$–$C_4$) alkoxy group, the alkyl moiety of which can be straight-chain or branched, include methoxy, ethoxy, n-propoxy, isopropoxy, n-butoxy, sec-butoxy and tert-butoxy. Halogen includes fluorine, chlorine, bromine and iodine.

In the compounds of formula (III), examples of the ($C_1$–$C_4$)alkylsulfonyloxy groups include methanesulfonyloxy, ethanesulfonyloxy, propanesulfonyloxy, isopropylsulfonyloxy and butanesulfonyloxy. Examples of the arylsulfonyloxy group include phenylsulfonyloxy, p-toluenesulfonyloxy, naphthalenesulfonyloxy.

In the compounds of formulae (I) and (III), examples of the polyisoprene groups represented by the following formula (VI)

wherein n is as defined for formula (I) above, include geranylfarnesyl (n=5), farnesylfarnesyl (n=6), farnesylgeranylgeranyl (n=7), farnesylfarnesylgeranyl (n=8), solanesyl (n=9), decaprenyl (n=10), undecaprenyl (n=11) and dodecaprenyl (n=12).

The compounds of formula (I) may be converted, if desired, to the corresponding acid addition salts with pharmaceutically acceptable acids. The acid addition salts are included within the scope of this invention, which include the salts with inorganic acids such as hydrochloric acid, hydrobromic acid, sulfuric acid, nitric acid, phosphoric acid and the like, and the salts with organic acids such as acetic acid, lactic acid, fumaric acid, citric acid, maleic acid, phthalic acid, malic acid, tartaric acid or the like.

The compounds of formula (I) can be present in geometrical isomers, for example, cis/trans isomers, optical isomers, or racemates. In addition to those compounds of formula (I), metabolites induced from compounds of formula (I) and the metabolic precursors are included within the scope of this invention.

The optically active compound of formula (I) is obtained by resolving a racemate using an optically active acid as a resolving agent, or by stereospecific syntheses using an optically active starting material of which the absolute configuration was determined.

The compounds of formula (I) may be prepared by various conventional methods, for example, by reacting a compound of formula (II)

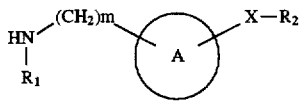 (II)

wherein m, A, X, R₁ and R₂ are as defined above, with a compound of formula (III)

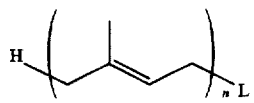 (III)

wherein n is as defined above, and L is a leaving group selected from the group consisting of halogen, $C_1$–$C_4$ alkylsulfonyloxy and arylsulfonyloxy.

This reaction is carried out in the presence or absence of solvents using 0.1–10 moles of a compound of formula (III) per mole of a compound of formula (II). In this reaction, various bases may be added, if necessary, which include carbonates such as potassium carbonate, sodium carbonate, sodium hydrogencarbonate; hydroxides such as sodium hydroxide, potassium hydroxide, lithium hydroxide; amines such as triethylamine, diethylamine, diisopropylethylamine, tributylamine, diisopropylamine, trimethylamine; pyridines such as pyridine, 4-dimethylaminopyridine. Diisopropylamine is preferably used.

Examples of compounds represented by formula (III) can include geranylfarnesyl chloride, farnesylfarnesyl chloride, farnesylgeranylgeranyl chloride, farnesylfarnesylgeranyl chloride, solanesyl chloride, decaprenyl chloride, undecaprenyl chloride, dodecaprenyl chloride, geranylfarnesyl bromide, farnesylfarnesyl bromide, farnesylgeranylgeranyl bromide, farnesylfarnesylgeranyl bromide, solanesyl bromide, decaprenyl bromide, undecaprenyl bromide, dodecaprenyl bromide, geranylfarnesyl iodide, farnesylfarnesyl iodide, farnesylgeranylgeranyl iodide, farnesylfarnesylgeranyl iodide, solanesyl iodide, decaprenyl iodide, undecaprenyl iodide, dodecaprenyl iodide, geranylfarnesyl methanesulfonate, farnesylfarnesyl methanesulfonate, farnesylgeranylgeranyl methanesulfonate, farnesylfarnesylgeranyl methanesulfonate, solanesyl methanesulfonate, decaprenyl methanesulfonate, undecaprenyl methanesulfonate, dodecaprenyl methanesulfonate, geranylfarnesyl ethanesulfonate, farnesylfarnesyl ethanesulfonate, farnesylgeranylgeranyl ethanesulfonate, farnesylfarnesylgeranyl ethanesulfonate, solanesyl ethanesulfonate, decaprenyl ethanesulfonate, undecaprenyl ethanesulfonate, dodecaprenyl ethanesulfonate, geranylfarnesyl propanesulfonate, farnesylfarnesyl propanesulfonate, farnesylgeranylgeranyl propanesulfonate, farnesylfarnesylgeranyl propanesulfonate, solanesyl propanesulfonate, decaprenyl propanesulfonate, undecaprenyl propanesulfonate, dodecaprenyl propanesulfonate, geranylfarnesyl butanesulfonate, farnesylfarnesyl butanesulfonate, farnesylgeranylgeranyl butanesulfonate, farnesylfarnesylgeranyl butanesulfonate, solanesyl butanesulfonate, decaprenyl butanesulfonate, undecaprenyl butanesulfonate, dodecaprenyl butanesulfonate, geranylfarnesyl isopropylsulfonate, farnesylfarnesyl isopropylsulfonate, farnesylgeranylgeranyl isopropylsulfonate, farnesylfarnesylgeranyl isopropylsulfonate, solanesyl isopropylsulfonate, decaprenyl isopropylsulfonate, undecaprenyl isopropylsulfonate, dodecaprenyl isopropylsulfonate, geranylfarnesyl p-toluenesulfonate, farnesylfarnesyl p-toluenesulfonate, farnesylgeranylgeranyl p-toluenesulfonate, farnesylfarnesylgeranyl p-toluenesulfonate, solanesyl p-toluenesulfonate, decaprenyl p-toluenesulfonate, undecaprenyl p-toluenesulfonate, dodecaprenyl p-toluenesulfonate.

The solvents employed in this reaction are not specifically limited, unless giving an influence on the reaction, which can include hydrocarbons such as benzene, toluene, xylene, hexane, and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; sulforan; pyridines such as pyridine, 4-dimethylaminopyridine; water; and these mixed solvents.

The reaction may be carried out at a temperature broadly ranging from ice-cooling to reflux-heating. The reaction time can be varied, depending on a reagent and a reaction temperature, etc., but is usually 0.5 to 36 hours. This reaction is preferably carried out at a temperature of 10° to 30° C. for 5 to 36 hours in the solvent such as ethers. More preferably, this reaction is carried out at a temperature of 10° to 25° C. for 12 to 24 hours in tetrahydrofuran.

The compounds of formula (II) may be prepared by various conventional methods, for example, by reacting a compound of formula (VII)

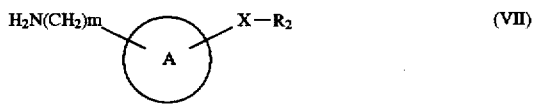 (VII)

wherein m, A, X and R₂ are as defined for formula (I) above, with a compound of formula (VIII)

R₃CHO (VIII)

wherein R₃ is a phenyl group which may be substituted by 1 to 5 substituents selected from hydroxy, ($C_1$–$C_4$)alkyl, ($C_1$–$C_4$)alkoxy and halogen, to prepare a compound of formula (IX)

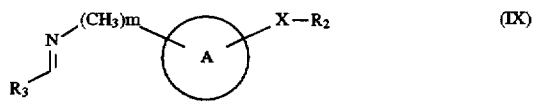 (IX)

wherein m, A, X and R₂ are as defined for formula (I) above, and R₃ are as defined for formula (VIII) above (Step A), followed by reducing a compound of formula (IX) (Step B).

Step A is the step of preparing a compound of formula (IX), and this reaction is usually carried out in the presence of the solvent. The reaction may be carried out while removing a producing water with Dean-Stark apparatus, etc., or in the presence of dehydrating agents such as anhydrous sodium carbonate, anhydrous potassium carbonate, anhydrous sodium sulfate, anhydrous potassium chloride, anhydrous magnesium sulfate, or molecular sieves. The solvents employed in this reaction are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; sulforan; and these mixed solvents.

The reaction may be carried out at a temperature broadly ranging from ice-cooling to reflux-heating. The reaction time can be varied, depending on a reagent and a reaction temperature, etc., but is usually 0.5 to 24 hours. This reaction is preferably carried out at a temperature ranging from 0° C. to reflux-heating for 1 to 12 hours in the presence of the solvents such as hydrocarbons or alcohols. More preferably, this reaction is carried out at a temperature of 0° to 30° C. for 3 to 12 hours in methanol.

Step B is the step of reducing a compound of formula (IX) to prepare a compound of formula (II). The reaction is usually carried out in the presence of a reducing agent. The reducing agents which can be used include metal hydride such as lithium borohydride, sodium borohydride, sodium cyanoborohydride, lithium aluminum hydride and diisobutyl aluminum hydride. This reaction is usually carried out in the presence of the solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethyliphosphoric triamide; alcohols such as methanol, ethanol and isopropanol; sulfoxides such as dimethylsulfoxide; water; and these mixed solvents.

The reaction may be carried out at a temperature broadly ranging from ice-cooling to reflux-heating. The reaction time can be varied, depending on a reagent and a reaction temperature, etc., but is usually 0.5 to 24 hours. Preferably, this reaction is carried out at a temperature ranging from ice-cooling to 50° C. for 1 to 5 hours in the presence of sodium borohydride or sodium cyanoborohydride in the solvent such as alcohols.

Step B may be carried out under catalytic hydrogenation. In the catalytic hydrogenation, the reaction is usually carried out in the presence of a catalyst. The catalysts which can be used include the hydrogenation catalyst such as palladium-carbon, platinum oxide and palladium hydroxide. This reaction is usually carried out in the presence of the solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; water; organic acid esters such as methyl acetate and ethyl acetate; and these mixed solvents.

This reaction is carried out under hydrogen gas at atmospheric pressure or at medium to high pressure, or by using formic acid or salt of formic acid such as sodium formate and ammonium formate as a hydrogen doner. In the reaction, if necessary, an acid can be added, which can include inorganic acids such as hydrochloric acid, sulfuric acid, phosphoric acid and nitric acid; organic acids such as acetic acid, propionic acid; sulfonic acids such as methanesulfonic acid, toluenesulfonic acid and camphorsulfonic acid; and these mixed acids. The reaction time can be varied, depending on a reagent and a reaction temperature, etc., but is usually 1 to 24 hours. Preferably, this reaction is carried out using palladium-carbon as the catalyst under hydrogen gas at atmospheric pressure at a temperature of 0° to 50° C. for 1 to 12 hours in the solvent such as alcohols.

The reactions in the above Steps A and B may be optionally carried out in the same vessel. More specifically, a compound of formula (VII) and a compound of formula (VIII) are reacted in a solvent to give a compound of formula (IX) which is then reduced with a reducing agent in the same vessel to give a compound of formula (II). The reducing agents which can be used include metal hydride such as lithium borohydride, sodium borohydride, sodium cyanoborohydride, lithium aluminum hydride and diisobutyl aluminum hydride. The solvents used are not specifically limited, unless giving an influence on the reaction, which can include hydrocarbons such as benzene, toluene, xylene, hexane and heptane; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; organic acid esters such as methyl acetate and ethyl acetate; organic acids such as acetic acid; and these mixed solvents. Preferably, this reaction is carried out by reacting a compound of formula (VII) with a compound of formula (VIII) at a temperature ranging from 0° to 30° C. for 1 to 12 hours in alcohols such as methanol and ethanol, to afford a compound of formula (IX) which is then reacted in the same vessel with a reducing agent such as sodium borohydride and sodium cyanoborohydride at a temperature ranging from 0° to 30° C. for 1 to 5 hours.

Reduction may be carried out by catalytic hydrogenation. In the catalytic hydrogenation, the reaction is usually carried out in the presence of a catalyst. The catalysts which can be used include the hydrogenation catalyst such as palladium-carbon, platinum oxide and palladium hydroxide. This reaction is usually carried out in the presence of the solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; water; organic acid esters such as methyl acetate and ethyl acetate; and these mixed solvents.

This reaction is carried out under hydrogen gas at atmospheric pressure or at medium to high pressure, or by using formic acid or salt of formic acid such as sodium formate and ammonium formate as a hydrogen doner. In the reaction, if necessary, an acid can be added, which can include inorganic acids such as hydrochloric acid, sulfuric acid, phosphoric acid and nitric acid; organic acids such as acetic acid and propionic acid; sulfonic acids such as methanesulfonic acid, toluenesulfonic acid and camphorsulfonic acid; and these mixed acids. The reaction time can be varied, depending on a reagent and a reaction temperature, etc., but is usually 1 to 24 hours. Preferably, this reaction is carried out using palladium-carbon as the catalyst under hydrogen gas at atmospheric pressure at a temperature of 0° to 50° C. for 1 to 12 hours in the solvent such as alcohols.

The compounds of formula (II) wherein X is $-(CH_2)_p$ NH— and $R_1$ and $R_2$ are each benzyl group having the same substituents can be prepared by reacting a compound of formula (X)

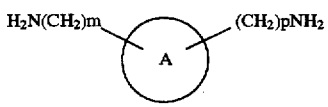

wherein m, A and p are as defined for formula (I) above, with a compound of formula (VIII)

R₃CHO    (VIII)

wherein R₃ is as defined above to prepare a compound of formula (XI)

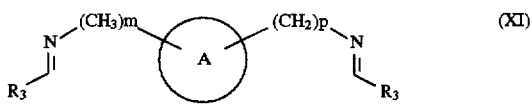

wherein m, A and p are as defined for formula (I) above, and R₃ is as defined for formula (VIII) above (Step C), followed by reduction (Step D).

Step C is the step of preparing a compound of formula (XI), which is usually carried out in the presence of the solvent. This reaction may be carried out while removing a producing water with Dean-Stark apparatus etc., or in the presence of dehydrating agents such as anhydrous sodium carbonate, anhydrous potassium carbonate, anhydrous sodium sulfate, anhydrous potassium chloride, anhydrous magnesium sulfate and molecular sieve. The solvents employed in this reaction are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; sulforan; and these mixed solvents.

The reaction may be carried out at a temperature broadly ranging from ice-cooling to reflux-heating. The reaction time can be varied, depending on a reagent and a reaction temperature etc., but is usually 0.5 to 24 hours. This reaction is preferably carried out at a temperature ranging from 0° C. to reflux-heating for 1 to 12 hours in the presence of the solvents such as hydrocarbons or alcohols. More preferably, this reaction is carried out at a temperature of 0° to 300° C. for 3 to 12 hours in methanol.

Step D is the step of reducing a compound of formula (IX) to prepare a compound of formula (II). The reaction is usually carried out by reducing in the presence of a reducing agent or by hydrogenation in the presence of a catalyst. The reducing agents which can be used include metal hydride such as lithium borohydride, sodium borohydride, sodium cyanoborohydride, lithium aluminum hydride and diisobutyl aluminum hydride. This reaction is usually carried out in the presence of the solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; water; and these mixed solvents.

The reaction may be carried out at a temperature broadly ranging from ice-cooling to reflux-heating. The reaction time can be varied, depending on a reagent and a reaction temperature, etc., but is usually 0.5 to 24 hours. Preferably, this reaction is carried out at a temperature ranging from ice-cooling to 50° C. for 1 to 5 hours in the presence of sodium borohydride or sodium cyanoborohydride in the solvent such as alcohols.

In the catalytic hydrogenation, the reaction is carried out in the presence of a catalyst. The catalysts which can be used include the hydrogenation catalyst such as palladium-carbon, platinum oxide and palladium hydroxide. The solvents used are not specifically limited, unless giving an influence on the reaction, which can include hydrocarbons such as benzene, toluene, xylene, hexane and heptane; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; organic acid esters such as methyl acetate and ethyl acetate; and these mixed solvents.

This reaction is carried out under hydrogen gas at atmospheric pressure or at medium to high pressure, and preferably hydrogen gas at atmospheric pressure is used.

The reaction time can be varied, depending on a reagent and a reaction temperature, etc., but is usually 0.5 to 24 hours. Preferably, this reaction is carried out using platinum oxide under hydrogen gas at atmospheric pressure at a temperature of 0° to 50° C. for 0.5 to 12 hours in the solvent such as alcohols, in particular methanol or ethanol.

The reactions in the above Steps C and D may be optionally carried out in the same vessel. More specifically, a compound of formula (X) and a compound of formula (VIII) can be reacted in a solvent to give a compound of formula (XI) which is then reduced with a reducing agent or subjected to catalytic reduction in the presence of a catalyst in the same vessel to give a compound of formula (II). The reducing agents which can be used include metal hydride such as lithium borohydride, sodium borohydride, sodium cyanoborohydride, lithium aluminum hydride and diisobutyl aluminum hydride. This reaction is usually carried out in the presence of the solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; water; and these mixed solvents. The reaction may be carried out at a temperature broadly ranging from ice-cooling to reflux-heating. The reaction time can be varied, depending on a reagent and a reaction temperature, etc., but is usually 0.5 to 24 hours. Preferably, this reaction is carried out by reacting a compound of formula (X) with a compound of formula (VIII) at a temperature ranging from 0° to 30° C. for 1 to 12 hours in alcohols such as methanol or ethanol, to afford a compound of formula (XI) which is then reacted in the same vessel with a reducing agent such as sodium borohydride or sodium cyanoborohydride at a temperature of 0° to 30° C. for 1 to 5 hours. In the catalytic hydrogenation, the catalysts which can be used include the hydrogenation catalyst such as palladium-carbon, platinum oxide and palladium hydroxide. The solvents used are not specifically limited, unless giving an influence on the reaction, which can include hydrocarbons such as benzene, toluene, xylene, hexane and heptane; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; organic acid esters such as methyl acetate and ethyl acetate; organic acids such as acetic acid; and these mixed solvents. This reaction is carried out under hydrogen gas at atmospheric pressure or at medium to high pressure, and preferably hydrogen gas at atmospheric pressure is used. The reaction time can be varied, depending on a reagent and a reaction temperature, etc., but is usually 0.5 to 24 hours. This reaction is preferably carried out by using platinum oxide or palladium-carbon as a catalyst in the presence of acetic acid under hydrogen gas at atmospheric pressure at a temperature of 0° to 50° C. for 3 to 12 hours in the solvent such as alcohols, in particular methanol or ethanol.

The invention provides a pharmaceutical composition comprising as an active ingredient a compound of formula (I) or a pharmaceutically acceptable salt thereof, and optionally a pharmaceutically acceptable carrier.

The present compounds of formula (I) can usually be administered in various dosage forms which include the preparations adapted for oral or parenteral administration. The oral preparations include tablets, hard and soft capsules, granules, powders, syrups, elixirs. The parenteral preparations include injections (intravenous, intramuscular, subcutaneous, intraperitoneal), drops and suppositories. These preparations can be prepared by conventional methods employing conventional additives such as excipients, binders, disintegrants, lubricants, flavorings, solubilizing aids, suspending agents, coating agents or the like. Routes and dosage of administration for the compounds of the invention are not specifically limited and are appropriately chosen depending upon the form of the preparations, age, sex, and weight of the patient, severity of the disease and other factors. Daily dosage of the active ingredient for adult is 0.1 to 600 mg. No adverse toxicological effects are indicated at any of the above dosage range.

This invention is further illustrated by the following examples which include Preparation Examples, Examples, Pharmacological Examples and Pharmaceutical Examples. The Preparation Examples will illustrate the synthesis of the starting materials and intermediates for the production of the present compounds, and the Examples will illustrate the production of the present compounds. The Pharmacological Examples will illustrate the pharmacological effects of the present compounds, and the Pharmaceutical Examples will illustrate pharmaceutical preparations which comprise the present compound as an active ingredient.

EXAMPLE 1 trans-N,N'-bis(3,4-dimethoxybenzyl)-N-solanesyl-1,2-diaminocyclohexane

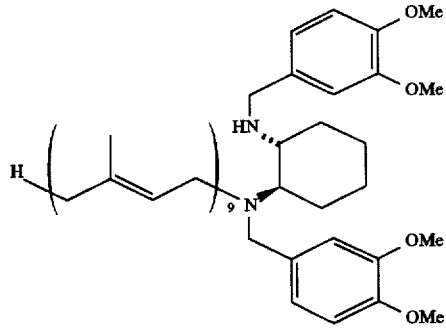

To a solution of trans-N,N'-bis(3, 4-dimethoxybenzyl)-1,2-diaminocyclohexane (10.36 g, 25 mmol) in tetrahydrofuran (50 ml) was added dropwise at room temperature a solution of solanesylbromide (3.47 g, 5 mmol) in tetrahydrofuran (10 ml). After the mixture was stirred at room temperature for 24 hours, the solvent was distilled off under reduced pressure. To the residue was added hexane (300 ml), and washed with acetonitrile (50 ml×3). The solvent was distilled off under reduced pressure from the hexane layer. A silica gel column chromatography of the residue gave 3.0 g of the title compound.

Yield=29%, free base: $^1$H NMR (CDCl$_3$)δ1.00–1.25(m, 4H), 1.60(s, 27H), 1.68(s, 3H), 1.50–1.85(m, 5H), 1.88–2.18 (m, 32H), 2.42–2.56(m, 2H), 3.01(d, J=6.5 Hz, 2H), 3.29(d, J=13.5 Hz, 1H), 3.49(d, J=12.5 Hz, 1H), 3.62(s, 3H), 3.68(d, J=12.5 Hz, 1H), 3.81(s, 3H), 3.84(s, 3H), 3.85(s, 3H), 3.80–3.86(d, J=13.5 Hz, 1H), 5.06–5.15(m, 8H), 5.17(t, J=6.5 Hz, 1H), 6.72–6.85(m, 6H)

The title compound was converted to the dihydrochloride by conventional method.

EXAMPLE 2 trans-N,N'-bis(3,4,5-trimethoxybenzyl)-N-solanesyl-1,2-diaminocyclohexane

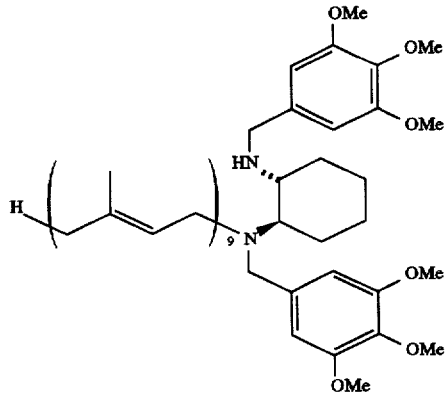

The title compound was prepared by a similar way as in Example 1, except for using trans-N,N'-bis(3, 4,5-trimethoxybenzyl)-1,2-diaminocyclohexane instead of trans-N,N'-bis(3,4-dimethoxybenzyl)-1,2-diaminocyclohexane.

Yield=67%, free base: $^1$H NMR (CDCl$_3$) δ1.00–1.25(m, 4H), 1.60(s, 27H), 1.68(s, 3H), 1.50–1.85(m, 5H), 1.90–b 2.15(m, 32H), 2.43–2.57(m, 2H), 3.05(d, J=6.5 Hz, 2H), 3.30(d, J=14.0 Hz, 1H), 3.48(d, J=12.6 Hz, 1H), 3.64(s, 6H), 3.70(d, J=14.0 Hz, 1H), 3.78(s, 6H), 3.79(s, 3H), 3.82(s, 3H), 3.82(d, J=12.6 Hz, 1H), 5.06–5.15(m, 8H), 5.22(t, J=6.5 Hz, 1H), 6.47 (s, 2H), 6.52(s, 2H)

The title compound was converted to the dihydrochloride by conventional method.

EXAMPLE 3 cis-N,N'-bis(3,4-dimethoxybenzyl)-N-solanesyl-1,2-diaminocyclohexane

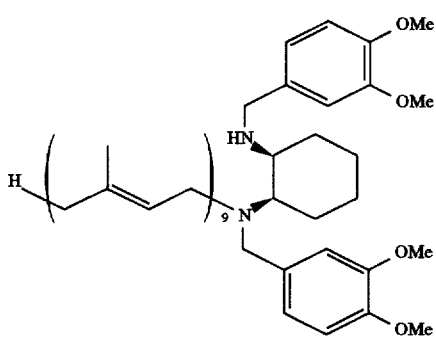

The title compound was prepared by a similar way as in Example 1, except for using cis-N,N'-bis(3, 4-dimethoxybenzyl)-1,2-diaminocyclohexane instead of trans-N,N'-bis(3,4-dimethoxybenzyl)-1,2-diaminocyclohexane.

Yield=39%, free base: $^1$H NMR (CDCl$_3$) δ1.15–1.35(m, 4H), 1.44(s, 3H), 1.60(s, 24H), 1.68(s, 3H), 1.50–1.82(m, 5H), 1.85–2.11(m, 32H), 2.55–2.63(m, 1H), 2.98–3.04(m, 1H), 3.12(d, J=6.5 Hz, 2H), 3.45(d, J=13.0 Hz, 1H), 3.60(s, 3H), 3.73(s, 3H), 3.76(d, J=13.0 Hz, 1H), 3.80(s, 3H), 3.84(s, 3H), 3.85(s, 3H), 5.06–5.15(m, 8H), 5.26(t, J=6.5 Hz, 1H), 6.73–6.87(m, 6H)

The title compound was converted to the dihydrochloride by conventional method.

EXAMPLE 4

1-(3,4-dimethoxybenzyl)-3-[N,N-(3,4-dimethoxybenzyl)-solanesylamino]pyrrolidine

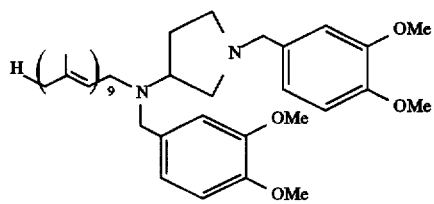

The title compound was prepared by a similar way as in Example 1, except for using 1-(3,4-dimethoxybenzyl)-3-[N-(3, 4-dimethoxybenzyl)amino]pyrrolidine instead of trans-N,N'-bis(3,4-dimethoxybenzyl)-1,2-diaminocyclohexane.

Yield=35%, free base: $^1$H NMR (CDCl$_3$) δ1.60(s, 27H), 1.68(s, 3H), 1.85–2.10(m, 34H), 2.45–2.67(m, 4H), 3.05(d, J=6.5 Hz, 2H), 3.40–3.64(m, 5H), 3.86(s, 6H), 3.87(s, 3H), 5.05–5.15(m, 8H), 5.25(t, J=6.5 Hz, 1H), 6.75–6.91(m, 6H)

The title compound was converted to the dihydrochloride by conventional method.

EXAMPLE 5

Endo-9-aza-9-benzyl-7-[N,N-(3,4-dimethoxybenzyl)-solanesyl]amino-3-oxabicyclo[3.3.1]nonane.

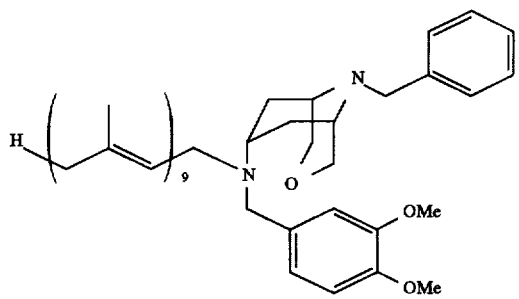

To a solution of endo-9-aza-9-benzyl-7-[N-(3, 4-dimethoxybenzyl)]amino-3-oxabicyclo[3.3.1]nonane (1.27 g) in tetrahydrofuran (50 ml) was added dropwise solanesylbromide (2.99 g, 4.31 mmol) at room temperature and the mixture was stirred for 1.5 hours. To the reaction solution was added 1% (w/v) aqueous potassium carbonate and extracted with ethyl acetate. The organic layer was washed with saturated brine, dried over anhydrous sodium sulfate, and the solvent was distilled off under reduced pressure. The residue was dissolved in hexane, washed with acetonitrile, and the solvent was distilled off under reduced pressure from the hexane layer. The residue was subjected to a silica gel column chromatography to give 360 mg of the title compound.

Free base: IR(film)$v_{max}$cm$^{-1}$ 2928, 2846, 1593, 1515, 1453, 1383, 1265, 1235, 1155, 1134, 1035; $^1$H NMR (CDCl$_3$) δ1.60(s, 27H), 1.64(s, 3H), 1.68(s, 3H), 1.73–1.76 (m, 2H), 1.97–2.06(m, 34H), 2.80–2.83(m, 2H), 3.14 (d, J=6 Hz, 2H), 3.27(d, J=11 Hz, 2H), 3.62(s, 2H), 3.86–3.93(m, 4H), 3.87(s, 3H), 3.88(s, 3H), 5.09–5.13(m, 9H), 5.27–5.29 (m, 1H), 6.81(d, J=8 Hz, 1H), 6.88(d, J=8 Hz, 1H), 6.97(d, J=2 Hz, 1H), 7.22–7.29(m, 5H)

The title compound was converted to the dihydrochloride by conventional method to give a pale yellow amorphous product.

EXAMPLE 6

N-{[N-(3,4-dimethoxybenzyl)]-3-aminopropyl}-N'-{[N-(3, 4-dimethoxybenzyl)-N-solanesyl]-3-aminopropyl}piperazine

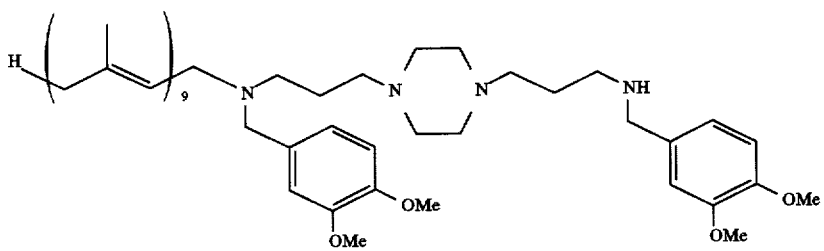

Example 5 was repeated except that N,N'-bis{[N-(3, 4-dimethoxybenzyl)]-3-aminopropyl}piperazine was used instead of endo-9-aza-9-benzyl-7-[N-(3,4-dimethoxybenzyl)]-amino-3-oxabicyclo [3.3.1]nonane, to give 1.03 g (37%) of the crude title compound. The crude title compound was converted to the tetrahydrochloride by conventional method, and recrystallized from acetone, to give 1.13 g of the tetrahydrochloride of the title compound as a yellow crystal.

Free base: $^1$H NMR (CDCl$_3$) δ1.60(s, 24H), 1.68(s, 3H), 1.90–2.10(m, 32H), 2.25–2.78(m, 12H), 3.03(d, J=6.4 Hz, 2H), 3.47(s, 2H), 3.74(s, 2H), 3.86(s, 6H), 3.87(s, 3H), 3.89(s, 3H), 5.10–5.13(m, 8H), 5.28(t, J=6.4 Hz, 1H), 6.77–6.91(m, 6H)

Tetrahydrochloride: m.p. 163° –171° C.

EXAMPLE 7

N,N'-bis(3,4-dimethoxybenzyl)-N-solanesyl-1,3-xylylene diamine

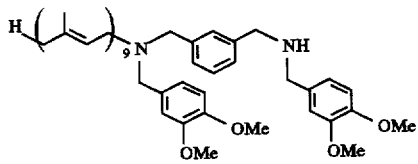

To a solution of N,N'-bis(3,4-dimethoxybenzyl)-1, 3-xylylene diamine (4.55 g, 10.4 mmol) in tetrahydrofuran (50 ml) was added dropwise at room temperature a solution of solanesylbromide (1.81 g, 2.61 mmol) in tetrahydrofuran (15 ml), and the mixture was stirred for 19 hours. The reaction mixture was diluted with ethyl acetate, washed with water and saturated brine in turn. The organic layer was dried over anhydrous potassium carbonate and the solvent was distilled off under reduced pressure. The residue was subjected to a silica gel column chromatography to give 2.10 g of the title compound as a pale yellow oily product.

Yield=77%, free base: $^1$H NMR (CDCl$_3$) δ1.57(s, 3H), 1.60(s, 27H), 1.89–2.11(m, 32H), 3.02(d, J=6.3 Hz, 2H), 3.50(s, 2H), 3.54(s, 2H), 3.74(s, 2H), 3.79(s, 2H), 3.85(s, 3H), 3.86(s, 3H), 3.87(s, 3H), 3.88(s, 3H), 5.01–5.19(m, 8H), 5.34(brt, J=6.8 Hz, 1H), 6.72–6.97(m, 7H), 7.16–7.32 (m, 3H)

The title compound was converted to the dihydrochloride by conventional method.

EXAMPLE 8

N,N'-bis(3,4-dimethoxybenzyl)-N-solanesyl-2,7-diaminofluorene

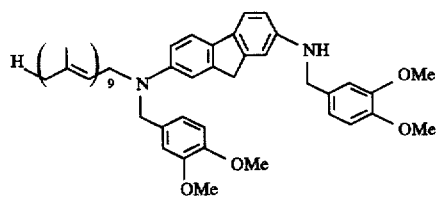

The title compound was prepared by a similar way as in Example 1, except for using N,N'-bis(3, 4-dimethoxybenzyl)-2,7-diaminofluorene instead of trans-N,N'-bis(3,4-dimethoxybenzyl)-1,2-diaminocyclohexane.

Yield=25%, free base: $^1$H NMR (CDCl$_3$) δ1.60(s, 24H), 1.68(s, 6H), 1.93–2.13(m, 32H), 3.70–4.05(m, 16H), 4.45–4.55(m, 2H), 5.05–5.15(m, 8H), 5.27–5.35(m, 1H), 6.55–7.05(m, 7H), 7.15–7.65(m, 5H)

The title compound was converted to the dihydrochloride by conventional method.

EXAMPLE 9

(1R, 2R)-N,N'-bis(3,4-dimethoxybenzyl)-N-solanesyl-1,2-diaminocyclohexane

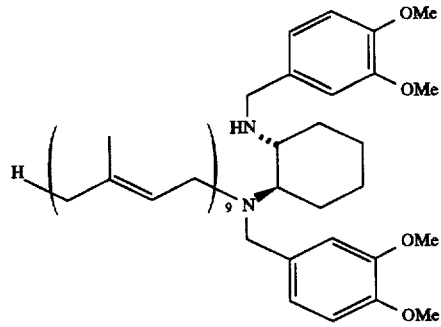

The title compound was prepared by a similar way as in Example 1, except for using (1R, 2R)-N,N'-bis(3, 4-dimethoxybenzyl)-1,2-diaminocyclohexane instead of trans-N,N'-bis(3,4-dimethoxybenzyl)-1,2-diaminocyclohexane.

Yield=46%, $[\alpha]_D^{27}$=−5.0° (c 1.01, ethanol) Other spectral data agreed with that of Example 1.

The title compound was converted to the dihydrochloride by conventional method.

$[\alpha]_D^{27}$=+20.1° (c 1.00, ethanol)

EXAMPLE 10

(1S, 2S)-N,N'-bis(3,4-dimethoxybenzyl)-N-solanesyl-1,2-diaminocyclohexane

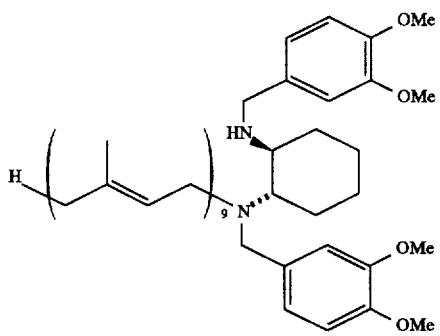

The title compound was prepared by a similar way as in Example 1, except for using (1S, 2S)-N,N'-bis(3,4-dimethoxybenzyl)-1, 2-diaminocyclohexane instead of trans-N,N'-bis(3,4-dimethoxybenzyl)-1,2-diaminocyclohexane.

Yield=47%, $[\alpha]_D^{27}$=+5.40° (c 1.00, ethanol) Other spectral data agreed with that of Example 1.

The title compound was converted to the dihydrochloride by conventional method.

$[\alpha]_D^{27}$=−20.60° (c 1.03, ethanol)

EXAMPLE 11 trans-N,N'-bis(3,4-dimethoxybenzyl)-N-geranylfarnesyl-1,2-diaminocyclohexane

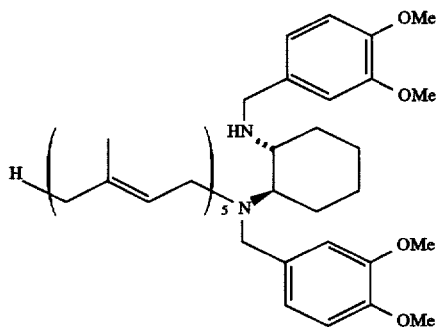

The title compound was prepared by a similar way as in Example 1, except for using geranylfarnesyl bromide instead of solanesyl bromide.

Yield=41%, free base: $^1$H NMR (CDCl$_3$) d 1.00–1.40 (m, 4H), 1.54–1.83 (m, 21H), 1.88–2.15 (m, 18H), 2.41–2.55 (m, 2H), 3.01 (d, J=6.3 Hz, 2H), 3.28 (d, J=14.1 Hz, 1H), 3.49 (d, J=13.0 Hz, 1H), 3.62 (s, 3H), 3.69 (d, J=13.0 Hz, 1H), 3.80 (s, 3H), 3.84 (s, 3H), 3.85 (s, 3H), 3.80 –3.85 (m, 1H), 5.05–5.13 (m, 4H), 5.16–5.22 (m, 1H), 6.71 –6.83 (m, 6H)

The title compound was converted to the dihydrochloride by conventional method.

Dihydrochloride: $^1$H NMR (CDCl$_3$) d 0.80–1.40 (m, 4H), 1.45 –1.74 (m, 20H), 1.75–2.40 (m, 18H), 3.25–3.38 (m, 1H), 3.50–3.65 (m, 2H), 3.87 (s, 3H), 3.90 (s, 3H), 3.99 (s, 6H), 3.80–4.00 (m, 1H), 4.20–4.90 (m, 4H), 4.95–5.22 (m, 4H), 5.70–5.90 (m, 1H), 6.70–7.15 (m, 4H), 7.50–7.80 (m, 2H), 10.48 (brs, 1H), 11.64 (brs, 1H), 11.88 (brs, 1H)

EXAMPLE 12 trans-N,N'-bis(3,4-dimethoxybenzyl)-N-farnesylgeranyl-geranyl-1, 2-diaminocyclohexane

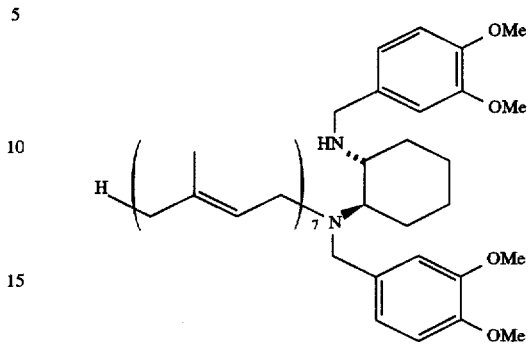

The title compound was prepared by a similar way as in Example 1, except for using farnesylgeranylgeranyl bromide instead of solanesyl bromide.

Yield=76%, free base: $^1$H NMR (CDCl$_3$) d 1.00–1.40 (m, 4H), 1.54–1.83 (m, 27H), 1.88–2.15 (m, 26H), 2.41–2.55 (m, 2H), 3.01 (d, J=6.3 Hz, 2H), 3.28 (d, J=14.1 Hz, 1H), 3.49 (d, J=13.0 Hz, 1H), 3.62 (s, 3H), 3.69 (d, J=13.0 Hz, 1H), 3.80 (s, 3H), 3.84 (s, 3H), 3.85 (s, 3H), 3.80 –3.85 (m, 1H), 5.05–5.13 (m, 6H), 5.16–5.22 (m, 1H), 6.71 –6.83 (m, 6H)

The title compound was converted to the dihydrochloride by conventional method.

Dihydrochloride: $^1$H NMR (CDCl$_3$) d 0.80–1.40 (m, 4H), 1.45 –1.74 (m, 26H), 1.75–2.40 (m, 26H), 3.25–3.38 (m, 1H), 3.50–3.65 (m, 2H), 3.87 (s, 3H), 3.90 (s, 3H), 3.99 (s, 6H), 3.80–4.00 (m, 1H), 4.20–4.90 (m, 4H), 4.95–5.22 (m, 6H), 5.70–5.90 (m, 1H), 6.70–7.15 (m, 4H), 7.50–780 (m, 2H), 10.48 (brs, 1H), 11.64 (brs, 1H), 11.88 (brs, 1H)

EXAMPLE 13 trans-N,N'-bis(3,4-dimethoxybenzyl)-N-farnesylfarnesyl-geranyl-1, 2-diaminocyclohexane

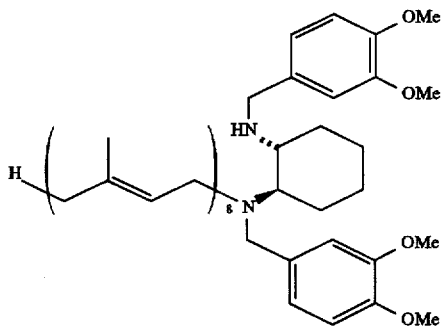

The title compound was prepared by a similar way as in Example 1, except for using farnesylfarnesylgeranyl bromide instead of solanesyl bromide.

Yield=39%, free base: $^1$H NMR (CDCl$_3$) d 1.00–1.40 (m, 4H), 1.54–1.83 (m, 30H), 1.88–2.15 (m, 30H), 2.41–2.55 (m, 2H), 3.01 (d, J=6.3 Hz, 2H), 3.28 (d, J=14.1 Hz, 1H), 3.49 (d, J=13.0 Hz, 1H), 3.62 (s, 3H), 3.69 (d, J=13.0 Hz, 1H), 3.80 (s, 3H), 3.84 (s, 3H), 3.85 (s, 3H), 3.80 –3.85 (m, 1H), 5.05–5.13 (m, 7H), 5.16–5.22 (m, 1H), 6.71 –6.83 (m, 6H)

The title compound was converted to the dihydrochloride by conventional method.

Dihydrochloride: $^1$H NMR (CDCl$_3$) d 0.80–1.40 (m, 4H), 1.45 –1.74 (m, 29H), 1.75–2.40 (m, 30H), 3.25–3.38 (m, 1H), 3.50–3.65 (m, 2H), 3.87 (s, 3H), 3.90 (s, 3H), 3.99 (s, 6H), 3.80–4.00 (m, 1H), 4.20–4.90 (m, 4H), 4.95–5.22 (m, 7H), 5.70–5.90 (m, 1H), 6.70–7.15 (m, 4H), 7.50 –7.80 (m, 2H), 10.48 (brs, 1H), 11.64 (brs, 1H), 11.88 (brs, 1H)

EXAMPLE 14 trans-N,N'-bis(3,4-dimethoxybenzyl)-N-decaprenyl-1,2-diaminocyclohexane

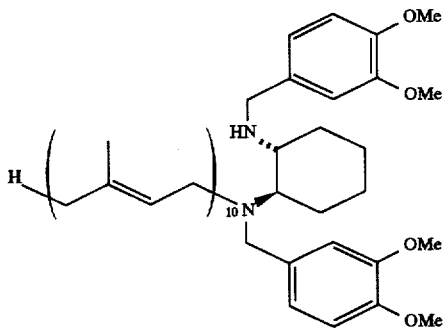

The title compound was prepared by a similar way as in Example 1, except for using decaprenyl bromide instead of solanesyl bromide.

Yield 65%, free base: $^1$H NMR (CDCl$_3$) d 1.00–1.26 (m, 5H), 1.50–1.85 (m, 4H), 1.60 (s, 30H), 1.68 (s, 3H), 1.90 –2.13 (m, 36H), 2.45–2.50 (m, 2H), 3.01 (d, J=6.4 Hz, 2H), 3.29 (d, J=13.7 Hz, 1H), 3.49 (d, J=12.7 Hz, 1H), 3.62 (s, 3H), 3.68 (d, J=13.7 Hz, 1H), 3.81 (s, 3H), 3.81 (d, J=12.7 Hz, 1H), 3.84 (s, 3H), 3.85 (s, 3H), 5.07 –5.13 (m, 9H), 5.18 (t, J=6.4 Hz, 1H), 6.72–6.82 (m, 6H)

The title compound was converted to the dihydrochloride by conventional method.

EXAMPLE 15 trans-N,N'-bis(3,4-dimethoxybenzyl)-N-dodecaprenyl-1,2-diaminocyclohexane

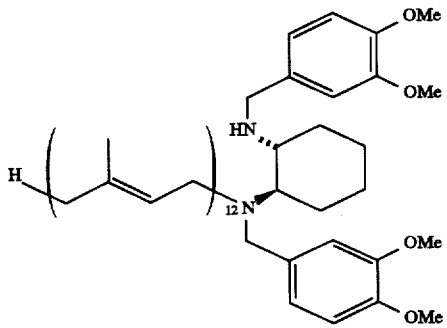

The title compound was prepared by a similar way as in Example 1, except for using dodecaprenyl bromide instead of solanesyl bromide.

Yield=71%, free base: $^1$H NMR (CDCl$_3$) d 1.00–1.26 (m, 5H), 1.50–1.85 (m, 4H), 1.60 (s, 36H), 1.68 (s, 3H), 1.90 –2.13 (m, 44H), 2.45–2.50 (m, 2H), 3.01 (d, J=6.4 Hz, 2H), 3.29 (d, J=13.7 Hz, 1H), 3.49 (d, J=12.7 Hz, 1H), 3.62 (s, 3H), 3.69 (d, J=13.7 Hz, 1H), 3.81 (s, 3H), 3.81 (d, J=12.7 Hz, 1H), 3.84 (s, 3H), 3.85 (s, 3H), 5.08 –5.13 (m, 11H), 5.19 (t, J=6.4 Hz, 1H), 6.72–6.82 (m, 6H)

The title compound was converted to the dihydrochloride by conventional method.

EXAMPLE 16 trans-N, N'-bis(4-methylbenzyl)-N-solanesyl-1,2-diaminocyclohexane

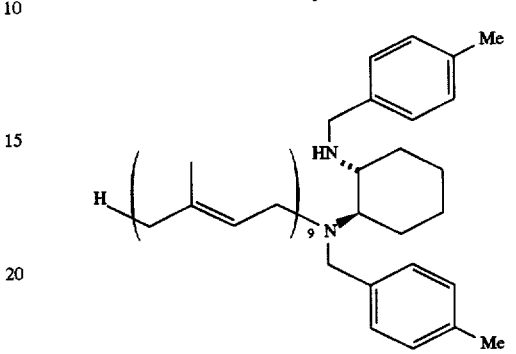

The title compound was prepared by a similar way as in Example 1, except for using trans-N, N'-bis(4-methylbenzyl)-1, 2-diaminocyclohexane instead of trans-N,N'-bis(3,4-dimethoxybenzyl)-1,2-diaminocyclohexane.

Yield=83%, free base: $^1$H NMR (CDCl$_3$) d 0.99–1.23 (m, 4H), 1.53 (s, 3H), 1.68 (s, 3H), 1.49–1.69 (m, 28 H), 1.73 –1.79 (m, 1H), 1.87–2.14 (m, 32 H), 2.31 (s, 3H), 2.32 (s, 3H), 2.34–2.49 (m, 2H), 2.90–3.03 (m, 2H), 3.27 (d, J=14 Hz, 1H), 3.50 (d, J=13 Hz, 1H), 3.68 (d, J=14 Hz, 1H), 3.81 (d, J=13 Hz, 1H), 5.06–5.18 (m, 9H), 7.03 –7.17 (m, 8H)

The title compound was converted to the dihydrochloride by conventional method.

EXAMPLE 17 trans-N, N'-bis(4-isopropylbenzyl)-N-solanesyl-1,2-diaminocyclohexane

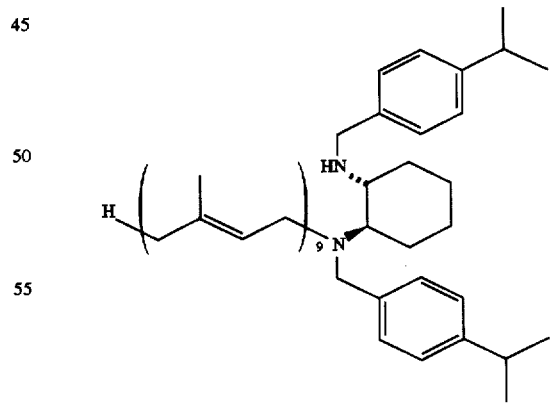

The title compound was prepared by a similar way as in Example 1, except for using trans-N, N'-bis(4-isopropylbenzyl)-1, 2-diaminocyclohexane instead of trans-N,N'-bis(3,4-dimethoxybenzyl)-1,2-diaminocyclohexane.

Yield=73%, free base: $^1$H NMR (CDCl$_3$) d 1.10–1.27 (m, 4H), 1.23 (d, J=6.8 Hz, 6H), 1.24 (d, J=6.8 Hz, 6H), 1.52 (s, 3H), 1.68 (s, 3H), 1.50–1.70 (m, 28 H), 1.73–1.80 (m, 1H), 1.87–2.17 (m, 32 H), 2.41–2.58 (m, 2H), 2.82–3.04 (m, 4H), 3.17 (d, J=14 Hz, 1H), 3.53 (d, J=13 Hz, 1H), 3.65 (d, J=14 Hz, 1H), 3.85 (d, J=11 Hz, 1H), 5.06 –5.21 (m, 9H), 7.08–7.20 (m, 8H)

The title compound was converted to the dihydrochloride by conventional method.

EXAMPLE 18 trans-N,N'-bis(4-fluorobenzyl)-N-solanesyl-1,2-diaminocyclohexane

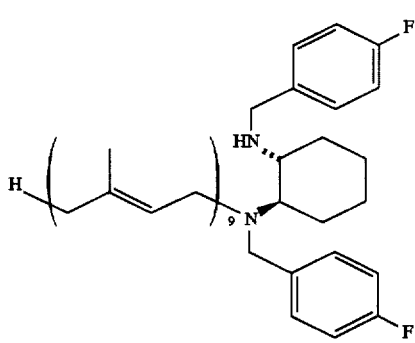

The title compound was prepared by a similar way as in Example 1, except for using trans-N,N'-bis(4-flurobenzyl)-1, 2-diaminocyclohexane instead of trans-N,N'-bis(3,4-dimethoxybenzyl)-1,2-diaminocyclohexane.

Yield=68%, free base: $^1$H NMR (CDCl$_3$) d 1.07–1.24 (m, 4H), 1.53 (s, 3H), 1.68 (s, 3H), 1.51–1.84 (m, 29 H), 1.86 –2.14 (m, 32 H), 2.38–2.55 (m, 2H), 2.88–3.03 (m, 2H), 3.32 (d, J=14 Hz, 1H), 3.52 (d, J=13 Hz, 1H), 3.64 (d, J=14 Hz, 1H), 3.86 (d, J=11 Hz, 1H), 5.06–5.15 (m, 9H), 6.92 (d, J=8.3 Hz, 2H), 6.97 (d, J=8.8 Hz, 2H), 7.14 –7.24 (m, 4H)

The title compound was converted to the dihydrochloride by conventional method.

EXAMPLE 19 trans-N,N'-bis(2,3-dichlorobenzyl)-N-solanesyl-1,2-diaminocyclohexane

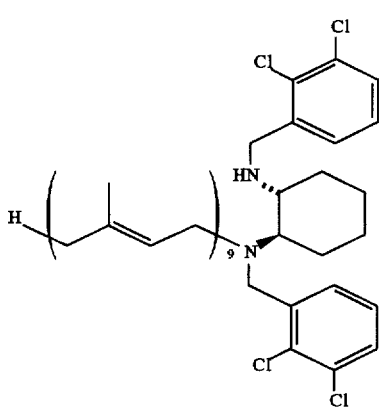

The title compound was prepared by a similar way as in Example 1, except for using trans-N,N'-bis(2,3-dichlorobenzyl)-1, 2-diaminocyclohexane instead of trans-N,N'-bis(3,4-dimethoxybenzyl)-1,2-diaminocyclohexane.

Yield=71%, free base: $^1$H NMR (CDCl$_3$) d 1.05–1.27 (m, 4H), 1.55–1.81 (m, 32H), 1.93–2.17 (m, 34H), 2.35–2.45 (m, 2H), 2.87 (dd, J=4, 14 Hz, 1H), 3.03 (dd, J=8, 14 Hz, 1H), 3.58 (d, J=15 Hz, 1H), 3.68 (t, J=14 Hz, 2H), 3.89 (d, J=15 Hz, 1H), 5.09–5.17 (m, 9H), 7.02–7.19 (m, 3H), 7.29–7.36 (m, 3H)

The title compound was converted to the dihydrochloride by conventional method.

EXAMPLE 20 trans-N,N'-bis(4-hydroxy-3-methoxybenzyl)-N-solanesyl-1,2-diaminocyclohexane

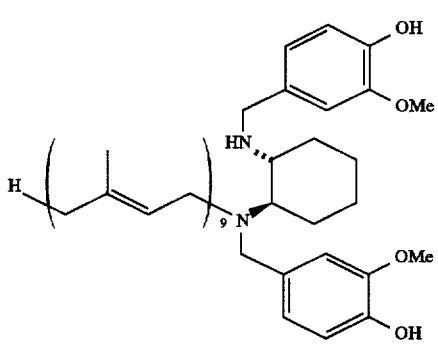

The title compound was prepared by a similar way as in Example 1, except for using trans-N,N'-bis(4-hydroxy-3-methoxybenzyl)-1, 2-diaminocyclohexane instead of trans-N,N'-bis(3,4-dimethoxybenzyl)-1,2-diaminocyclohexane.

Yield=62%, free base: $^1$H NMR (CDCl$_3$) d 1.09–1.23 (m, 4H), 1.56–1.78 (m, 32H), 1.83–2.06 (m, 34H), 2.45–2.55 (m, 2H), 3.00 (d, J=7 Hz, 2H), 3.27 (d, J=14 Hz, 1H), 3.45 (d, J=12 Hz, 1H), 3.56 (s, 3H), 3.64–3.70 (m, 1H), 3.77 (s, 3H), 3.83 (d, J=12 Hz, 1H), 5.07–5.13 (m, 8H), 5.16 –5.19 (m, 1H), 6.65–6.82 (m, 6H)

The title compound was converted to the dihydrochloride by conventional method.

EXAMPLE 21 trans-N,N'-bis(4-methoxybenzyl)-N-solanesyl-1,2-diaminocyclohexane

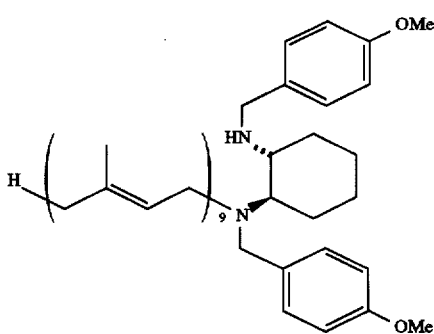

The title compound was prepared by a similar way as in Example 1, except for using trans-N,N'-bis(4-methoxybenzyl)-1, 2-diaminocyclohexane instead of trans-N,N'-bis(3,4-dimethoxybenzyl)-1,2-diaminocyclohexane.

Yield=72%, free base: $^1$H NMR (CDCl$_3$) d 1.12–1.17 (m, 4H), 1.53 (s, 3H), 1.60 (s, 24H), 1.68 (s, 3H), 1.75–2.10 (m, 36H), 2.39–2.47 (m, 2H), 2.95–2.97 (m, 2H), 3.25 (d, J=13.7 Hz, 1H), 3.49 (d, J=12.7 Hz, 1H), 3.64 (d, J=13.7 Hz, 1H), 3.81 (d, J=13.2 Hz, 1H), 3.78 (s, 6H), 5.08 –5.17 (m, 9H), 6.78–6.82 (m, 4H), 7.11–7.19 (m, 4H)

The title compound was converted to the dihydrochloride by conventional method.

$^1$H NMR (CDCl$_3$) d 1.24–1.49 (m, 4H), 1.59 (s, 3H), 1.60 (s, 24H), 1.67 (s, 3H), 1.74–2.29 (m, 38H), 3.60 (brs, 2H), 3.79 (s, 3H), 3.83 (s, 3H), 4.31 (d, J=13.2 Hz, 1H), 4.47 (d, J=12.2 Hz, 1H), 4.63 (d, J=12.7 Hz, 1H), 4.83 (br, 1H), 5.08–5.12 (m, 8H), 5.81 (brs, 1H), 6.92–6.96 (m, 4H), 7.61–7.73 (m, 4H), 10.49 (br, 1H), 11.65 (br, 1H), 11.81 (br, 1H)

EXAMPLE 22 trans-N,N'-bis(4-butoxybenzyl)-N-solanesyl-1,2-diaminocyclohexane

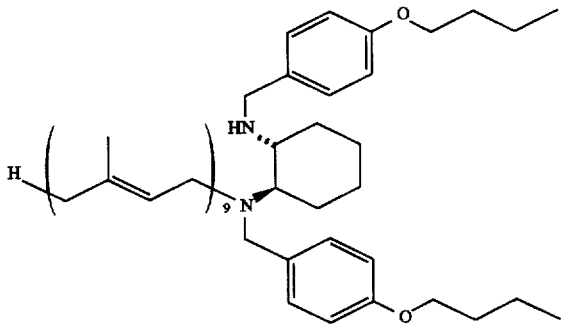

The title compound was prepared by a similar way as in Example 1, except for using trans-N,N'-bis(4-butoxybenzyl)-1, 2-diaminocyclohexane instead of trans-N,N'-bis(3,4-dimethoxybenzyl)-1,2-diaminocyclohexane.

Yield=82%, free base: $^1$H NMR (CDCl$_3$) d 0.98 (t, J=7.6 Hz, 6H), 0.99–1.17 (m, 4H), 1.44–0.52 (m, 4H), 1.53 (s, 3H), 1.60 (s, 24H), 1.68 (s, 3H), 1.72–1.79 (m, 4H), 1.88–2.06 (m, 36H), 2.41–2.44 (m, 2H), 2.94–2.96 (m, 2H), 3.24 (d, J=13.7 Hz, 1H), 3.48 (d, J=12.7 Hz, 1H), 3.63 (d, J=13.7 Hz, 1H), 3.81 (d, J=12.7 Hz, 1H), 3.93 (t, J=6.4 Hz, 4H), 5.10–5.13 (m, 9H), 6.77–6.81 (m, 4H), 7.10 (d, J=8.3 Hz, 2H), 7.16 (d, J=8.3 Hz, 2H)

The title compound was converted to the dihydrochloride by conventional method.

$^1$H NMR (CDCl$_3$) d 0.95–1.00 (m, 6H), 1.20–1.44 (m, 4H), 1.45–1.84 (m, 38H), 1.96–2.29 (m, 38H), 3.58 (brs, 2H), 3.92–3.99 (m, 4H), 4.29 (d, J=13.2 Hz, 1H), 4.46 (d, J=12.2 Hz, 1H), 4.63 (d, J=13.2 Hz, 1H), 4.85 (br, 1H), 5.07–5.13 (m, 8H), 5.83 (brs, 1H), 6.91–6.94 (m, 4H), 7.58–7.71 (m, 4H), 10.49 (br, 1H), 11.64 (br, 1H), 11.83 (br, 1H)

EXAMPLE 23 trans-N,N'-bis(2,3,4,5-tetramethoxy-6-methylbenzyl)-N-solanesyl-1,2-diaminocyclohexane

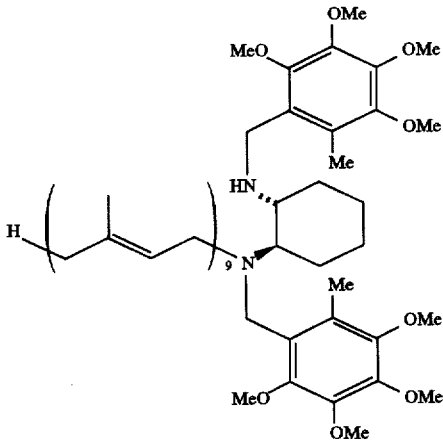

The title compound was prepared by a similar way as in Example 1, except for using trans-N,N'-bis(2,3,4,5-tetramethoxy- 6-methylbenzyl)-1,2-diaminocyclohexane instead of trans-N,N'-bis(3,4-dimethoxybenzyl)-1,2-diaminocyclohexane.

Yield=51%, free base: $^1$H NMR (CDCl$_3$) d 1.15–1.16 (m, 4H), 1.60 (s, 24H), 1.62 (s, 3H), 1.68 (s, 3H), 1.95–2.18 (m, 36H), 2.13 (s, 3H), 2.21 (s, 3H), 2.34–2.40 (m, 2H), 2.90–2.95 (m, 2H), 3.44 (d, J=12.2 Hz, 1H), 3.52 (d, J=11.7 Hz, 1H), 3.57 (d, J=12.2 Hz, 1H), 3.60 (s, 3H), 3.61 (d, J=11.7 Hz, 1H), 3.75 (s, 3H), 3.76 (s, 3H), 3.79 (s, 3H), 3.80 (s, 3H), 3.88 (s, 6H), 3.89 (s, 3H), 5.08–5.17 (m, 9H)

The title compound was converted to the dihydrochloride by conventional method.

$^1$H NMR (CDCl$_3$) d 0.90–1.75 (m, 34H), 1.88–2.45 (m, 44H), 3.48–4.99 (m, 30H), 5.09–5.13 (m, 9H), 10.27 (br, 1H), 10.71 (br, 1H), 11.08 (br, 1H)

EXAMPLE 24 trans-N,N'-bis(3,4-diethoxybenzyl)-N-solanesyl-1,4-diaminocyclohexane

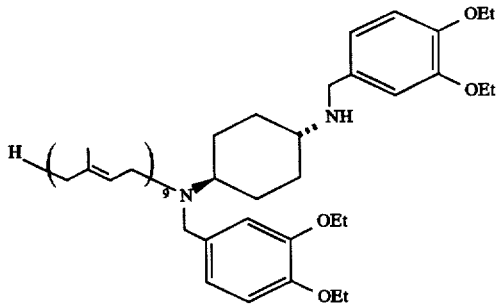

The title compound was prepared by a similar way as in Example 1, except for using trans-N,N'-bis(3,4-diethoxybenzyl)-1, 4-diaminocyclohexane instead of trans-N,N'-bis(3,4-dimethoxybenzyl)-1,2-diaminocyclohexane.

Yield 56%, free base : $^1$H NMR (CDCl$_3$) d 1.07–1.13 (m, 2H), 1.31–1.37 (m, 2H), 1.41–1.45 (m, 12H), 1.53–1.58 (m, 27H), 1.68 (s, 3H), 1.83 (d, J=11 Hz, 2H), 1.97–2.06 (m, 32H), 2.41 (t, J=10 Hz, 1H), 2.55 (t, J=8 Hz, 1H), 3.05 (d, J=7 Hz, 2H), 3.49 (s, 2H), 3.70 (s, 2H), 4.04–4.15 (m, 8H), 5.10–5.12 (m, 8H), 5.21 (t, J=6 Hz, 1H), 6.78 –6.92 (m, 6H)

The title compound was converted to the dihydrochloride by conventional method.

EXAMPLE 25

1-(2,3,4,5-tetramethoxy-6-methylbenzyl)-3-[N,N-(2, 3,4,5-tetramethoxy-6-methylbenzyl)solanesylamino] pyrrolidine

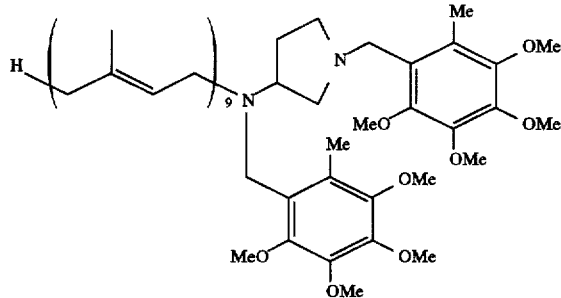

The title compound was prepared by a similar way as in Example 1, except for using 1-(2, 3,4,5-tetramethoxy-6-methylbenzyl)-3-[N-(2, 3,4,5-tetramethoxy-6-methylbenzyl)-amino]pyrrolidine instead of trans-N,N'-bis (3,4-dimethoxybenzyl)-1, 2-diaminocyclohexane.

Yield=24%, free base: $^1$H NMR (CDCl$_3$) d. 1.60 (s, 27H), 1.68 (s, 3H), 1.75–1.90 (m, 2H), 1.90–2.10 (m, 32H), 2.21 (s, 3H), 2.25 (s, 3H), 2.32–2.38 (m, 1H), 2.42–2.48 (m, 1H), 2.64–2.67 (m, 1H), 2.74–2.77 (m, 1H), 2.99 (d, J=6.4 Hz, 2H), 3.35–3.42 (m, 1H), 3.45–3.55 (m, 4H), 3.75 (s, 3H), 3.75 (s, 3H), 3.76 (s, 3H), 3.81 (s, 3H), 3.87 (s, 3H), 3.88 (s, 3H), 3.90 (s, 3H), 3.91 (s, 3H), 5.05–5.15 (m, 8H), 5.21 (t, J=6.4 Hz, 1H)

The title compound was converted to the dihydrochloride by conventional method.

EXAMPLE 26

1-(3,4-diethoxybenzyl)-3-[N,N-(3,4-diethoxybenzyl)-solanesylamino]pyrrolidine

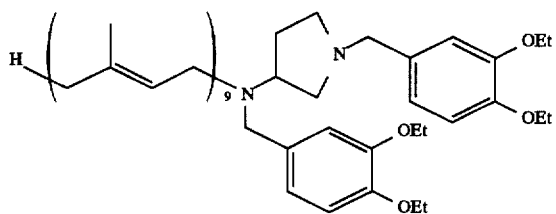

The title compound was prepared by a similar way as in Example 1, except for using 1-(3,4-diethoxybenzyl)-3-[N-(3, 4-diethoxybenzyl)amino]pyrrolidine instead of trans-N, N'-bis(3,4-dimethoxybenzyl)-1,2-diaminocyclohexane.

Yield=40%, free base: $^1$H NMR (CDCl$_3$) d 1.41–1.45 (m, 12H), 1.60 (s, 3H), 1.68 (s, 3H), 1.83–1.85 (m, 2H), 1.98 –2.06 (m, 32H), 2.45–2.61 (m, 4H), 3.03 (d, J=7 Hz, 2H), 3.40 (d, J=13Hz, 1H), 3.48 (d, J=14 Hz, 1H), 3.57 (dd, J=6 Hz, 15 Hz, 2H), 4.06–4.11 (m, 8H), 5.09–5.12 (m, 8H), 5.24 (t, J=7 Hz, 1H), 6.78 (d, J=2Hz, 3H), 6.87 (d, J=7Hz, 3H)

The title compound was converted to the dihydrochloride by conventional method.

EXAMPLE 27

1-(3,4-difluorobenzyl)-3-[N,N-(3,4-difluorobenzyl)-solanesylamino]pyrrolidine

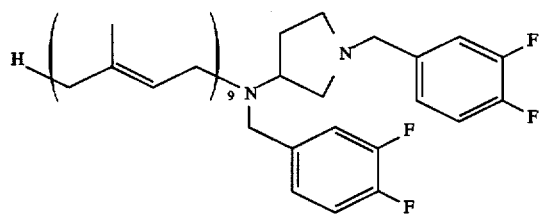

The title compound was prepared by a similar way as in Example 1, except for using 1-(3,4-difluorobenzyl)-3-[N-(3, 4-difluorobenzyl)amino]pyrrolidine instead of trans-N,N'-bis(3,4-dimethoxybenzyl)-1,2-diaminocyclohexane.

Yield=12%, free base: $^1$H NMR (CDCl$_3$) d 1.60 (s, 27H), 1.68 (s, 3H), 1.80 (m, 1H), 1.95–2.10 (m, 33H), 2.40–2.70 (m, 4H), 3.03 (d, J=5.8 Hz, 2H), 3.35–3.60 (m, 5H), 5.00 –5.15 (m, 8H), 5.19 (t, J=5.8 Hz), 6.90–7.20 (m, 6H)

The title compound was converted to the dihydrochloride by conventional method.

$^1$H NMR (CDCl$_3$) δ1.60 (s, 27H), 1.68 (s, 3H), 1.80–2.20 (m, 32H), 2.50–3.10 (m, 2H), 3.50–4.60 (m, 11H), 5.11 (m, 8H), 5.36 (m, 1H), 7.25 (m, 2H), 7.49 (m, 2H), 7.68 (m, 2H), 13.22 (m, 2H)

EXAMPLE 28

N-{[N-(2,3,4,5-tetramethoxy-6-methylbenzyl)]-3-aminopropyl }-N'-{[(N-2,3,4,5-tetramethoxy-6-methylbenzyl)- N-solanesyl]-3-aminopropyl } piperazine

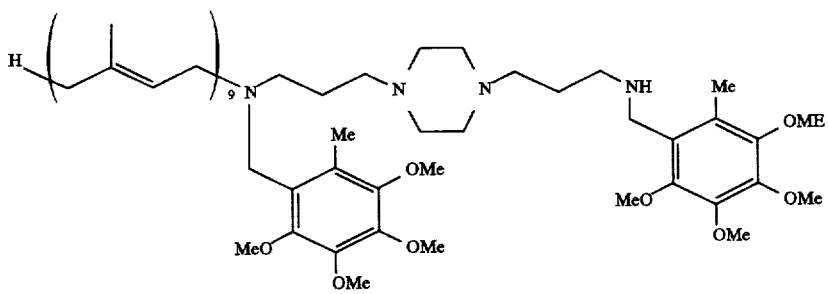

The title compound was prepared by a similar way as in Example 5, except for using N,N'-bis{[N-(2, 3,4,5-tetramethoxy-6-methylbenzyl)]-3-aminopropyl}piperazine instead of endo-9-aza-9-benzyl-7-[N-(3,4-dimethoxybenzyl)]-amino-3-oxabicyclo[3.3.1]nonane.

Yield=56%

The title compound was converted to the tetrahydrochloride by conventional method.

Tetrahydrochloride: m.p. 118°–122° C.

EXAMPLE 29

N-{[N-(3,4-diethoxybenzyl)]-3-aminopropyl}-N'-{[(N-3, 4-diethoxybenzyl)-N-solanesyl]-3-aminopropyl}piperazine

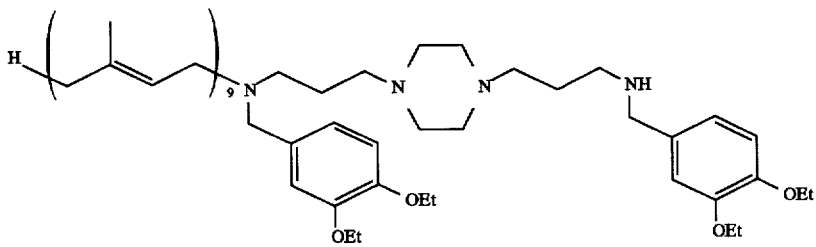

The title compound was prepared by a similar way as in Example 5, except for using N,N'-bis{[N-(3, 4-diethoxybenzyl)]-3-aminopropyl}piperazine instead of endo-9-aza-9-benzyl-7-[N-(3,4-dimethoxybenzyl)]amino-3-oxabicyclo[3.3.1]nonane.

Yield=56%, free base: $^1$H NMR (CDCl$_3$) d 1.42–1.45 (m, 12H), 1.58 (s, 27H), 1.58–1.72 (m, 4H), 1.68 (s, 3H), 1.97 –2.08 (m, 32H), 2.30 (t, J=5 Hz, 2H), 2.38–2.68 (m, 10H), 2.68 (bs, 2H), 3.02 (d, J=6 Hz, 2H), 3.45 (s, 2H), 3.71 (s, 2H), 4.04–4.10 (m, 8H), 5.09–5.13 (m, 8H), 5.27 (t, J=4Hz, 1H), 6.78 (s, 2H), 6.82 (s, 2H), 6.88 (s, 2H)

The title compound was converted to the tetrahydrochloride by conventional method.

EXAMPLE 30

N,N'-bis(3,4-difluorobenzyl)-N-solanesyl-1,3-xylylene diamine

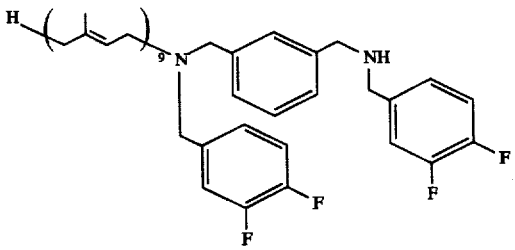

The title compound was prepared by a similar way as in Example 7, except for using N,N'-bis(3, 4-difluorobenzyl)-1,3-xylylene diamine instead of N,N'-bis(3,4-dimethoxybenzyl)-1,3-xylylene diamine.

Yield=17%, free base: $^1$H NMR (CDCl$_3$) d 1.55–1.59, (m, 27H), 1.67 (s, 3H), 1.92–2.07 (m, 32H), 2.99 (d, J=6.8 Hz 2H), 3.47 (s, 2H), 3.53 (s, 2H), 3.75 (s, 2H), 3.77 (s, 2H), 5.05–5.12 (m, 8H), 5.29 (t, J=6.8 Hz, 1H), 7.02 –7.12 (m, 4H), 7.18–7.27 (m, 6H)

The title compound was converted to the dihydrochloride by conventional method.

EXAMPLE 31

N,N'-bis(3,4-diethoxybenzyl)-N-solanesyl-1,3-xylylene diamine

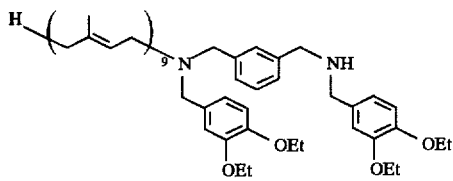

The title compound was prepared by a similar way as in Example 7, except for using N,N'-bis(3, 4-diethoxybenzyl)-1,3-xylylene diamine instead of N,N'-bis(3,4-dimethoxybenzyl)-1,3-xylylene diamine.

Yield=11%, free base: $^1$H NMR (CDCl$_3$) d 1.40–1.45 (m, 12H), 1.55–1.62 (m, 27H), 1.68 (s, 3H), 1.92–2.09 (m, 32H), 3.01 (d, J=6.8 Hz, 2H), 3.47 (s, 2H), 3.52 (s, 2H), 3.72 (s, 2H), 3.77 (s, 2H), 4.03–4.09 (m, 8H), 5.06–5.13 (m, 8H), 5.33 (t, J=6.8 Hz, 1H), 6.77–6.83 (m, 4H), 6.89 (s, 1H), 6.92–6.93 (m, 1H), 7.16–7.20 (m, 1H), 7.25 –7.26 (m, 2H), 7.29 (s, 1H)

The title compound was converted to the dihydrochloride by conventional method.

$^1$H NMR (DMSO-d6) d 1.30–1.35 (m, 12H), 3.99–4.09 (m, 16H), 6.93–6.96 (m, 2H), 7.00–7.02 (m, 2H), 7.28 (d, J=1.9 Hz, 2H), 7.47–7.51 (m, 1H), 7.61 (d, J=7.3 Hz, 2H), 7.66 (s, 1H), 9.70 (brs, 4H)

EXAMPLE 32

N,N'-bis(2,3,4,5-tetramethoxy-6-methylbenzyl)-N-solanesyl-1,3-xylylene diamine

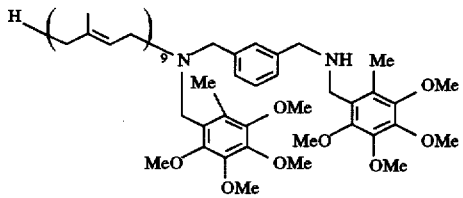

The title compound was prepared by a similar way as in Example 7, except for using N,N'-bis(2, 3,4,5-tetramethoxy-6-methylbenzyl)-1,3-xylylene diamine instead of N,N'-bis(3,4-dimethoxybenzyl)-1,3-xylylene diamine.

Yield=14%., free base: $^1$H NMR (CDCl$_3$ ) d 1.51–1.61 (m, 27H), 1.67 (s, 3H), 1.95–2.09 (m, 32H), 2.17 (s, 3H), 2.23 (s, 3H), 2.94 (d, J=6.8 Hz, 2H), 3.44 (s, 2H), 3.53 (s, 2H), 3.72 (s, 2H), 3.74 (s, 3H), 3.76 (s, 3H), 3.77–3.82 (m, 2H), 3.79 (s, 3H), 3.81 (s, 3H), 3.85 (s, 3H), 3.87 (s, 3H), 3.895 (s, 3H), 3.899 (s, 3H), 5.09–5.12 (m, 8H), 5.35 (t, J=6.8 Hz, 1H), 7.17–7.27 (m, 4H)

The title compound was converted to the dihydrochloride by conventional method.

PREPARATION EXAMPLE 1 trans-N,N'-bis(3,4-diethoxybenzyl)-1,2-diaminocyclohexane

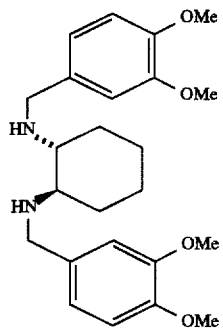

To a solution of veratraldehyde (16.6 g, 0.10 mol) in methanol (100 ml) was added at room temperature trans-1, 2-cyclohexane diamine (5.71 g, 0.05 mol) and the mixture was stirred for 12 hours. Then sodium borohydride (7.60 g, 0.20 mol) was added by portions and the mixture was further stirred at room temperature for 5 hours. The mixture was concentrated under reduced pressure, and water was added to the concentrate. After it was extracted with chloroform, the chloroform layer was washed twice with water and once with saturated brine, dried over anhydrous magnesium sulfate. The solvent was distilled off under reduced pressure to give the title compound as yellow oil. This product was used for a subsequent reaction without purification.

PREPARATION EXAMPLE 2 trans-N,N'-bis(3,4,5-trimethoxybenzyl)-1,2-diaminocyclohexane

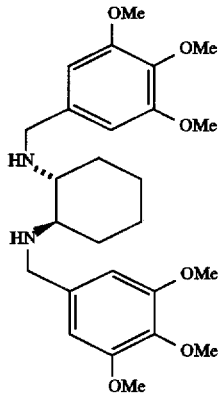

The title compound was prepared by a similar way as in Preparation Example 1, except for using 3,4,5-trimethoxybenzaldehyde instead of veratraldehyde.

PREPARATION EXAMPLE 3 cis-N,N'-bis(3,4-dimethoxybenzyl)-1,2-diaminocyclohexane

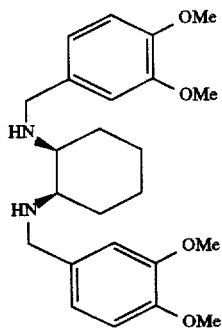

The title compound was prepared by a similar way as in Preparation Example 1, except for using cis-1,2-cyclohexane diamine instead of trans-1,2-cyclohexane diamine.

PREPARATION EXAMPLE 4

1-(3,4-dimethoxybenzyl)-3-[N-(3,4-dimethoxybenzyl)amino]-pyrrolidine

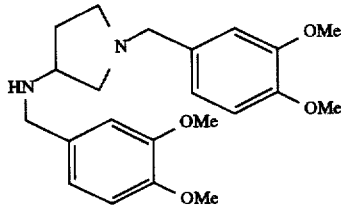

The title compound was prepared by a similar way as in Preparation Example 1, except for using 3-aminopyrrolidine instead of trans-1,2-cyclohexane diamine.

PREPARATION EXAMPLE 5

Endo-9-aza-9-benzyl-7-[N-(3,4-dimethoxybenzyl)] amino-3-oxabicyclo[3.3.1]nonane

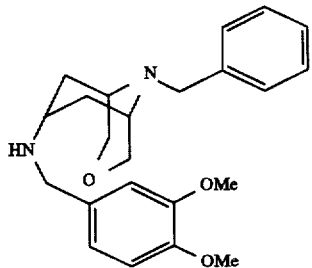

The title compound was prepared by a similar way as in Preparation Example 1, except for using endo-7-amino-9-aza-9-benzyl-3-oxabicyclo[3.3.1]nonane disclosed in Japanese Patent Kokai 7-10881 instead of trans-1,2-cyclohexane diamine.

PREPARATION EXAMPLE 6

N,N'-bis{[N-(3,4-dimethoxybenzyl)]-3-aminopropyl}piperazine

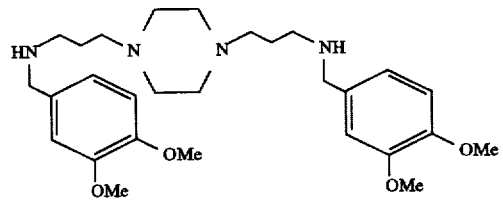

The title compound was prepared by a similar way as in Preparation Example 1, except for using 1,4-bis(3-aminopropyl)piperazine instead of trans-1,2-cyclohexane diamine.

PREPARATION EXAMPLE 7

N,N'-bis(3,4-dimethoxybenzyl)-2,7-diaminofluorene

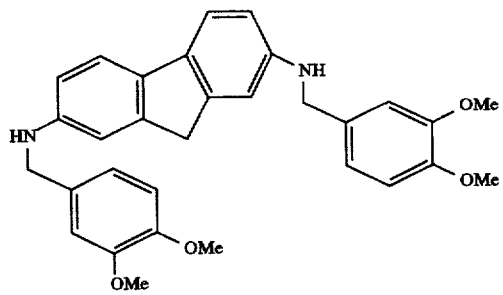

The title compound was prepared by a similar way as in Preparation Example 1, except for using 2,7-diaminofluorene instead of trans-1,2-cyclohexane diamine.

PREPARATION EXAMPLE 8

N,N'-bis(3,4-dimethoxybenzyl)-1,3-xylylene diamine

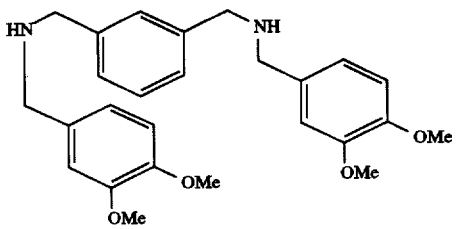

To a solution of m-xylylene diamine (10.0 g, 73.42 mmol) in methanol (300 ml) was added veratraldehyde (25.0 g, 150.50 mmol) and the mixture was stirred at room temperature for 10 minutes. The solvent was distilled off under reduced pressure. The residue was dissolved in benzene, and the solvent was distilled off under reduced pressure. This procedure was repeated twice. The residue was dissolved in methanol (200 ml), and sodium borohydride (5.83 g, 154.20 mmol) was added by portions over a period of 15 minutes under ice-cooling and the mixture was stirred for 30 minutes. After the mixture was further stirred at room temperature for 18 hours, acetone (10 ml) was added and the solvent was distilled off under reduced pressure. To the residue was added water (150 ml), which was then acidified with concentrated hydrochloric acid (20 ml) and stirred for one hour under ice-cooling. The precipitated crystal was collected by filtration and recrystallized from water to give 23.05 g (62%) of the title compound (dihydrochloride) as colorless crystals. A part of the dihydrochloride was dissolved in a 10%(w/v) aqueous solution of sodium hydroxide and extracted with chloroform. The organic layer was dried over anhydrous potassium carbonate and the solvent was distilled off under reduced pressure to give the title compound (free base).

Dihydrochloride: $^1$H NMR (DMSO-$d_6$) δ3.76(s, 6H), 3.77(s, 6H), 4.07(s, 4H), 4.09(s, 4H), 6.95(d, J=8.3 Hz, 2H), 7.05(dd, J=1.0 Hz, 6.8 Hz, 2H), 7.35(s, 2H), 7.49(t, J=7.3 Hz, 1H), 7.62(d, J=7.8 Hz, 2H), 7.69(s, 1H), 9.82(brs, 4H, replaced by heavy water)

Free base: $^1$H NMR (CDCl$_3$) δ1.60(s, 2H, replaced by heavy water), 3.76(s, 4H), 3.80(s, 4H), 3.87(s, 6H), 3.88(s, 6H), 6.81(d, J=8.3 Hz, 2H), 6.86(d, J=8.3 Hz, 2H), 6.90(s, 1H), 7.23(d, J=7.3 Hz, 2H), 7.27–7.40(m, 2H)

PREPARATION EXAMPLE 9

(1S,2S)-N,N'-bis(3,4-dimethoxybenzyl)-1,2-diaminocyclohexane

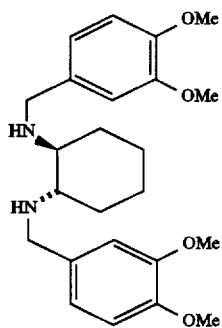

The title compound was prepared by a similar way as in Preparation Example 1, except for using (1S,2S)-1,2-diaminocyclohexane instead of trans-1,2-cyclohexane diamine.

Yield=87%

The analytical data of $^1$H NMR agreed with that of Preparation Example 1.

PREPARATION EXAMPLE 10

(1R,2R)-N,N'-bis(3,4-dimethoxybenzyl)-1,2-diaminocyclohexane

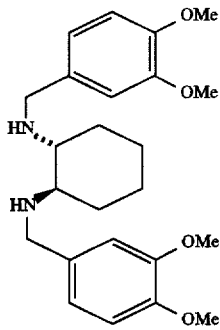

The title compound was prepared by a similar way as in Preparation Example 1, except for using (1R,2R)-1,2-diaminocyclohexane instead of trans-1,2-cyclohexane diamine.

Yield=100%

The analytical data of $^1$H NMR agreed with that of Preparation Example 1.

PREPARATION EXAMPLE 11 trans-N,N'-bis(4-methylbenzyl)-1,2-diaminocyclohexane

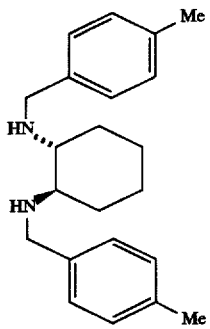

The title compound was prepared by a similar way as in Preparation Example 1, except for using 4-methylbenzaldehyde instead of veratraldehyde.

PREPARATION EXAMPLE 12 trans-N,N'-bis(4-isopropylbenzyl)-1,2-diaminocyclohexane

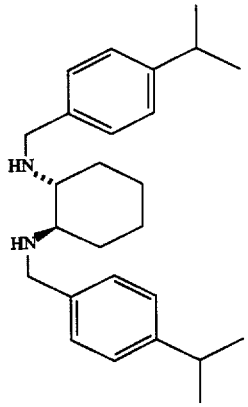

The title compound was prepared by a similar way as in Preparation Example 1, except for using 4-isopropylbenzaldehyde instead of veratraldehyde.

PREPARATION EXAMPLE 13 trans-N,N'-bis(4-fluorobenzyl)-1,2-diaminocyclohexane

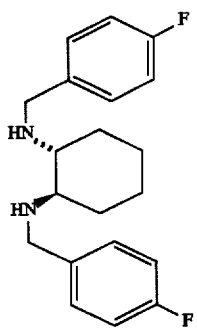

The title compound was prepared by a similar way as in Preparation Example 1, except for using 4-fluorobenzaldehyde instead of veratraldehyde.

PREPARATION EXAMPLE 14 trans-N,N'-bis(2,3-dichlorobenzyl)-1,2-diaminocyclohexane

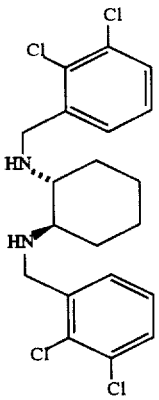

The title compound was prepared by a similar way as in Preparation Example 1, except for using 2,3-dichlorobenzaldehyde instead of veratraldehyde.

$^1$H NMR (CDCl$_3$) d 1.04–1.09 (m, 2H), 1.18–1.30 (m, 2H), 1.72–1.74 (m, 2H), 2.02–2.04 (m, 2H), 2.16 (d, J=14 Hz, 2H), 2.21–2.28 (m, 2H), 3.77 (d, J=14 Hz, 2H), 3.97 (d, J=14 Hz, 2H), 7.15 (t, J=8 Hz, 2H), 7.30–7.35 (m, 4H)

PREPARATION EXAMPLE 15 trans-N,N'-bis(4-hydroxy-3-methoxybenzyl)-1,2-diaminocyclohexane

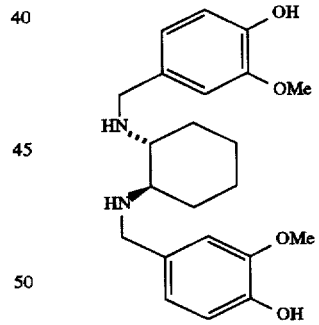

The title compound was prepared by a similar way as in Preparation Example 1, except for using vanillin instead of veratraldehyde.

$^1$H NMR (CDCl$_3$) d 1.15–1.27 (m, 4H), 1.74–1.76 (m, 2H), 2.16–2.19 (m, 2H), 2.35–2.38 (m, 2H), 3.56 (d, J=13 Hz, 2H), 3.72 (s, 6H), 3.87 (d, J=13 Hz, 2H), 6.72 (dd, J=1, 8 Hz, 2H), 6.77 (d, J=8 Hz, 2H), 6.85 (d, J=1 Hz, 2H)

PREPARATION EXAMPLE 16 trans-N,N'-bis(4-methoxybenzyl)-1,2-diaminocyclohexane

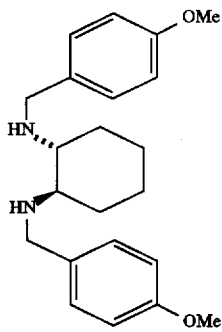

Preparation Example 1 was repeated except that 4-methoxybenzaldehyde was used instead of veratraldehyde, to give the title compound as a colorless needle.

Yield=67%, m.p. 110°–112° C.

¹H NMR (CDCl₃) d 1.01–1.03 (m, 2H), 1.19–1.24 (m, 2H), 1.70–1.72 (m, 2H), 1.81 (brs, 2H, replaced by heavy water), 2.13–2.16 (m, 2H), 2.22–2.24 (m, 2H), 3.58 (d, J =12.7 Hz, 2H), 3.79 (s, 6H), 3.83 (d, J=12.7 Hz, 2H), 6.84 (d, J=8.3 Hz, 4H), 7.22 (d, J=8.3 Hz, 4H)

PREPARATION EXAMPLE 17 trans-N,N'-bis(4-butoxybenzyl)-1,2-diaminocyclohexane

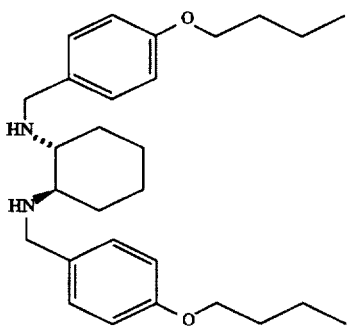

The title compound was prepared by a similar way as in Preparation Example 1, except for using 4-butoxybenzaldehyde instead of veratraldehyde.

Yield=81%

¹H NMR (CDCl₃) d 0.97 (t, J=7.3 Hz, 6H), 0.99–1.03 (m, 2H), 1.15–1.23 (m, 2H), 1.44–1.54 (m, 4H), 1.70–1.79 (m, 6H), 2.11–2.15 (m, 2H), 2.20–2.25 (m, 2H), 3.55 (d, J=12.7 Hz, 2H), 3.81 (d, J=12.7 Hz, 2H), 3.94 (t, J=6.4 Hz, 4H), 6.83 (d, J=8.3 Hz, 4H), 7.19 (d, J=8.3 Hz, 4H)

PREPARATION EXAMPLE 18 trans-N,N'-bis(2,3,4,5-tetramethoxy-6-methylbenzyl)-1,2-diaminocyclohexane

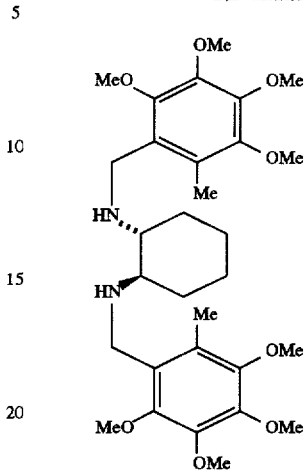

The title compound was prepared by a similar way as in Preparation Example 1, except for using 2,3,4,5-tetramethoxy-6-methyl benzaldehyde instead of veratraldehyde.

Yield=100%

¹H NMR (CDCl₃) d 1.06–1.08 (m, 2H), 1.23–1.33 (m, 2H), 1.75–1.78 (m, 2H), 2.16–2.19 (m, 2H), 2.18 (s, 6H), 2.28 –2.31 (m, 2H), 3.51 (d, J=11.7 Hz, 2H), 3.74 (s, 6H), 3.76 (s, 6H), 3.84 (d, J=11.2 Hz, 2H), 3.84 (s, 6H), 3.90 (s, 6H)

PREPARATION EXAMPLE 19 trans-N,N'-bis(3,4-diethoxybenzyl)-1,4-diaminocyclohexane

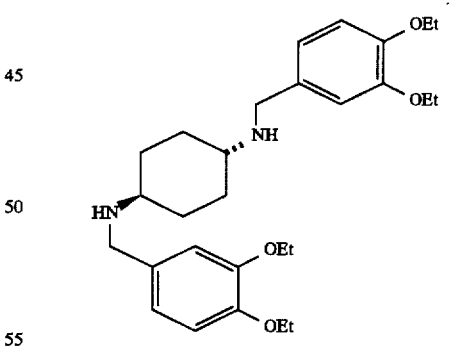

The title compound was prepared by a similar way as in Preparation Example 1, except that trans-1,4-cyclohexane diamine was used instead of trans-1,2-cyclohexane diamine and 3,4-diethoxybenzaldehyde was used instead of veratraldehyde.

Yield=47%

¹H NMR (CDCl₃) d 1.15 (t, J=10 Hz, 4H), 1.41 –1.48(m, 12H), 1.96 (d, J=6 Hz, 4H), 2.49 (bs, 2H), 3.72 (s, 4H), 4.07 (q, J=7Hz, 4H), 4.08 (q, J=7 Hz, 4H), 6.79 –6.86(m, 6H)

PREPARATION EXAMPLE 20

N,N'-bis(2,3,4,5-tetramethoxy-6-methylbenzyl)-3-aminopyrrolidine

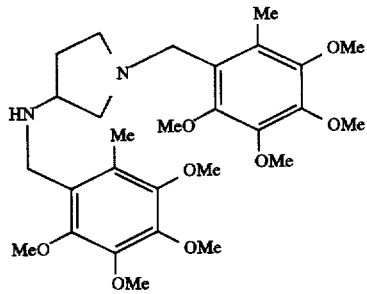

To a solution of 2,3,4,5-tetramethoxy-6-methylbenzaldehyde (12.7 g, 52.9 mmol) in methanol (100 ml) was added 3-aminopyrrolidine (2.0 g, 23.2 mmol) and the mixture was stirred under reflux-heating for 4 hours. After cooling the mixture to room temperature, sodium borohydride (2.0 g, 52.6 mmol) was added by portions and the mixture was stirred for 3 hours. After 5(w/v)% aqueous solution of sodium hydroxide was added to the reaction solution which was then extracted with ethyl acetate. The organic layer was washed with successive water and saturated brine and dried over anhydrous magnesium sulfate. The solvent was distilled off under reduced pressure, and a silica gel column chromatography of the residue gave 6.34 g of the title compound from the fraction of methanol/chloroform (1/19) eluent.

Yield=51%

PREPARATION EXAMPLE 21

N,N'-bis(3,4-diethoxybenzyl)-3-aminopyrrolidine

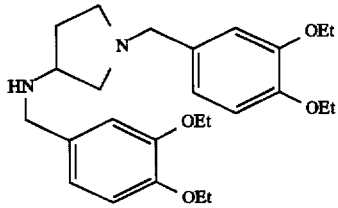

The title compound was prepared by a similar way as in Preparation Example 1, except that 3-aminopyrrolidine was used instead of trans-1,2-cyclohexane diamine and 3,4-diethoxybenzaldehyde was used instead of veratraldehyde.

Yield=76%

$^1$H NMR (CDCl$_3$) d 1.41–1.45 (m, 12H), 1.60–1.61 (m,1H), 2.10–2.15 (m, 1H), 2.38 (dd, J=5 Hz, 10 Hz, 1H), 2.50 (dd, J=8 Hz, 15 Hz, 1H), 2.62 (dd, J=8 Hz, 15 Hz, 1H), 2.72 (dd, J=7 Hz, 9 Hz, 1H), 3.30–3.35 (m, 1H), 3.49 (d, J=12 Hz, 1H), 3.55 (d, J=11 Hz, 1H), 3.64 (s, 2H), 4.03–4.10 (m, 8H), 6.80–6.90 (m, 6H)

PREPARATION EXAMPLE 22

N,N'-bis(3,4-difluorobenzyl)-3-aminopyrrolidine

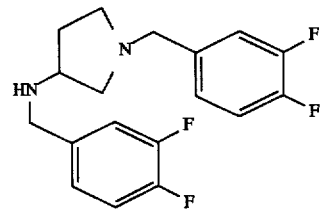

The title compound was prepared by a similar way as in Preparation Example 1, except that 3-aminopyrrolidine was used instead of trans-1,2-cyclohexane diamine and 3,4-difluorobenzaldehyde was used instead of veratraldehyde.

Yield=95%, free base: $^1$H NMR (CDCl$_3$) d 1.61 (m, 1H), 2.13 (m, 1H), 2.39 (m, 1H), 2.47 (m, 1H), 2.60–2.70 (m, 2H), 3.31 (m, 1H), 3.52 (d, J=13.2 Hz, 1H), 3.56 (d, J=13.2 Hz, 1H), 3.66 (d, J=13.7 Hz, 1H), 3.70 (d, J=13.7 Hz, 1H), 6.90–7.20 (m, 6H)

PREPARATION EXAMPLE 23

N,N'-bis{[N-(2,3,4,5-tetramethoxy-6-methylbenzyl)]-3-aminopropyl}piperazine

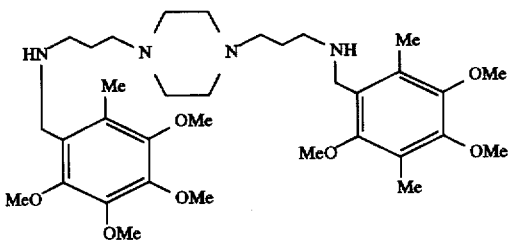

The title compound was prepared by a similar way as in Preparation Example 1, except that 1,4-bis(3-aminopropyl)piperazine was used instead of trans-1,2-cyclohexane diamine and 2,3,4,5-tetramethoxy-6-methylbenzaldehyde was used instead of veratraldehyde.

$^1$H NMR (CDCl$_3$) d 1.67–1.74 (m, 4H), 2.23 (s, 6H), 2.36–2.64 (m, 12H), 2.68 (t, J=6.8 Hz, 4H), 3.70 (s, 4H), 3.78 (s, 6H), 3.84 (s, 6H), 3.89 (s, 6H), 3.90 (s, 6H)

PREPARATION EXAMPLE 24

N,N'-bis{[N-(3,4-diethoxybenzyl)]-3-aminopropyl}piperazine

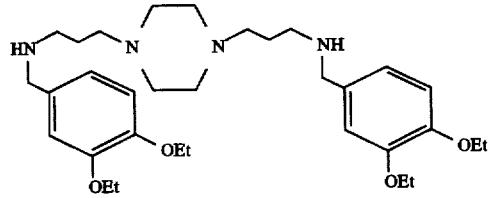

The title compound was prepared by a similar way as in Preparation Example 1, except that 1,4-bis(3-aminopropyl)piperazine was used instead of trans-1,2-cyclohexane diamine and 3,4-diethoxybenzaldehyde was used instead of veratraldehyde.

Yield=80%, free base: $^1$H NMR (CDCl$_3$) d 1.41–1.46 (m, 12H), 1.70 (sept, J=7Hz, 4H), 2.38 (t, J=7 Hz, 4H), 2.35 –2.58 (m, 4H), 2.66 (t, J=7 Hz, 4H), 3.70 (s, 4H), 4.05 –4.12 (m, 4H), 6.81 (d, J=1 Hz, 4H), 6.87(s, 2H)

PREPARATION EXAMPLE 25

N,N'-bis(3,4-difluorobenzyl)-1,3-xylylene diamine

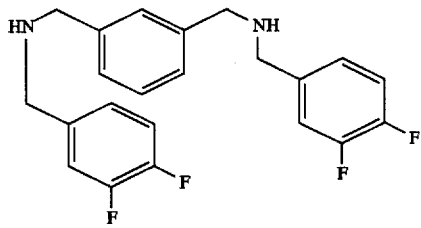

The title compound was prepared by a similar way as in Preparation Example 8, except for using 3,4-difluorobenzaldehyde instead of veratraldehyde.

$^1$H NMR (CDCl$_3$) d 3.76–3.81 (m, 8H), 7.04–7.13 (m, 4H), 7.16–7.36 (m, 6H)

PREPARATION EXAMPLE 26

N,N'-bis(3,4-diethoxybenzyl)-1,3-xylylene diamine

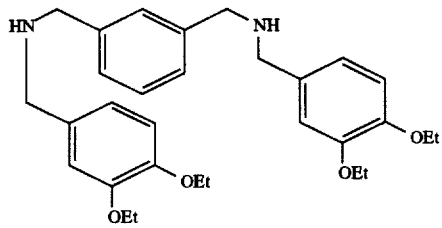

The title compound was prepared by a similar way as in Preparation Example 8, except for using 3,4-diethoxybenzaldehyde instead of veratraldehyde.

PREPARATION EXAMPLE 27

N,N'-bis(2,3,4,5-tetramethoxy-6-methylbenzyl)-1,3-xylylene diamine

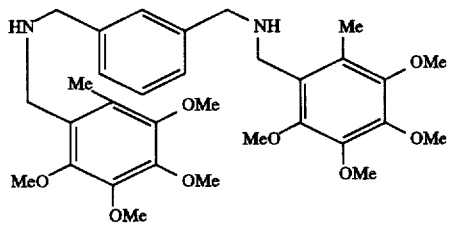

The title compound was prepared by a similar way as in Preparation Example 8, except for using 2,3,4,5-tetramethoxy-6-methylbenzaldehyde instead of veratraldehyde.

PREPARATION EXAMPLE 28

2,3,4,5-tetramethoxy-6-methylbenzaldehyde

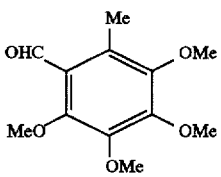

To a solution of 1,2,3,4-tetramethoxy-5-methylbenzene (34.3 g, 162 mmol) in trifluoroacetic acid (200 ml) was added hexamethylenetetramine (25.0 g, 178 mmol), and the solution was heated under reflux for 3 hours. The solvent was distilled off under reduced pressure. Water (200 ml) was added to the residue which was then heated under reflux for one hour, neutralized with 3N sodium hydroxide and extracted with ethyl acetate (200 ml×3), and dried over anhydrous magnesium sulfate. The solvent was distilled off under reduced pressure. The residue was subjected to a silica gel column chromatography to give 34.9 g of the title compound.

Yield=90%

$^1$H NMR (CDCl$_3$) d 2.46 (s, 3H), 3.76 (s, 3H), 3.91 (s, 3H), 3.95 (s, 3H), 10.43 (s, 1H)

The pharmacological activities of compounds of the present invention as agents for overcoming a multidrug resistance and agents for enhancing the activity of anti-cancer agents are illustrated below in detail.

PHARMACOLOGICAL EXAMPLE 1

Colony formation assay for adriamycin resistant cells (MCF 7/ADM) derived from human breast cancer.

A culture solution of adriamycin resistant cells (MCF 7/ADM) derived from human breast cancer, suspended in MEM (minimal essential medium, available from Nissui Seiyaku) containing 10% fetal calf serum, glutamine (2 µg/ml) and kanamycin (50 µg/ml), was prepared so as to give a concentration of 750 cells/ml. The solution was dispensed into a 12 well-microplate so as to give 1500 cells per well. The cells was incubated at 37° C. for 24 hours in 5% CO$_2$. A 0.50 mmol solution of each test compounds in dimethylsulfoxide was added cumulatively, and the cells were incubated at 37° C. for a week in 5% CO$_2$. After colonies were stained with 0.1% methylene blue in methanol for 30 minutes, and dried, the number of colonies was counted by a microscope. The concentration of the compound required to inhibit 30% colony formation of cells, expressed by IC$_{30}$, was calculated from the counted number of colonies. The results are shown in the following Table 1.

TABLE 1

| Colony formation assay | |
|---|---|
| Test compound | IC$_{30}$ (µM) |
| Compound of Example 1 (dihydrochloride) | 50 |
| Compound of Example 4 (dihydrochloride) | 50 |
| Compound of Example 5 (dihydrochloride) | 50 |
| Compound of Example 7 (dihydrochloride) | 20 |
| Compound of formula (V) (dihydrochloride) | 5 |

The above results indicate that the compounds of the present invention have clearly lower cytotoxicity, as compared with a compound of formula (V).

PHARMACOLOGICAL EXAMPLE 2

Combined effect of the present compounds and adriamycin on adriamycin non-resistant cells,(MCF 7/WT) derived from human breast cancer.

A culture solution of adriamycin non-resistant cells (MCF 7/WT) derived from human breast cancer in MEM (minimal essential medium, available from Nissui Seiyaku) containing 10% fetal calf serum, glutamine (2 µg/ml) and kanamycin (50 µg/ml), was dispensed into a 12 well-microplate so as to give 1000 cells per well. The cells were incubated at 37° C. for 24 hours in 5% $CO_2$. Adriamycin was cumulatively added to the culture solution at a range of 0–50 ng/ml, and a solution of each test compound in dimethylsulfoxide was further added such that a final concentration becomes the $IC_{30}$ obtained in Pharmacological Example 1. The cells were incubated at 37° C. for a week in 5% $CO_2$. As a control, adriamycin alone was added to the culture solution as described above and the cells were incubated for a week in the same manner. After colonies were stained with 0.1% methylene blue in methanol for 30 minutes and dried, the number of colonies was counted by a microscope. The concentrations of the compound required to inhibit 50% colony formation of cells, expressed by $IC_{50}$, are calculated from the counted number of colonies. Further, there was determined a potentiation activity, which is a relative value based on $IC_{50}$ value obtained for the control(administration of adriamycin alone).

The results are shown in the following Table 2.

TABLE 2

Combined effect of present compound and adriamycin on MCF 7/WT

| Test compound | Combined concentration (µM) | ADM $IC_{50}$ (ng/ml) | Potentiation activity |
|---|---|---|---|
| (RUN 1) | | | |
| Control (ADM) | — | 10 | 1.0 |
| Compound of Example 1 (dihydrochloride) | 50 | 5.2 | 0.52 |
| Compound of Example 6 (dihydrochloride) | 1 | 6.2 | 0.62 |
| (RUN 2) | | | |
| Control (ADM) | — | 3.6 | 1.0 |
| Compound of Example 4 (dihydrochloride) | 50 | 2.0 | 0.56 |

The above results indicate that the compounds of the present invention enhance anti-cancer activity of adriamycin in ADM non-resistant cells derived from human breast cancer.

PHARMACOLOGICAL EXAMPLE 3

Combined effect of the present compounds and adriamycin on adriamycin resistant cells (MCF 7/ADM) derived from human breast cancer.

A culture solution of adriamycin resistant cells (MCF 7/ADM) derived from human breast cancer in MEM (minimal essential medium, available from Nissui Seiyaku) containing 10% fetal calf serum, glutamine (2 µg/ml) and kanamycin (50 µg/ml), was dispensed into a 12 well-microplate so as to give 1500 cells per well. The cells were incubated at 37° C. for 24 hours in 5% $CO_2$. Adriamycin was cumulatively added to the culture solution at a range of 0–5000 ng/ml, and a solution of each test compound in dimethylsulfoxide was further added such that a final concentration becomes the $IC_{30}$ obtained in Pharmacological Example 1. The cells was incubated at 37° C. for a week in 5% $CO_2$. As a control, adriamycin alone was added to the culture solution as described above and the cells were incubated for a week in the same manner. After colonies were stained with 0.1% methylene blue in methanol for 30 minutes and dried, the number of colonies was counted by a microscope. The concentrations of the compound required to inhibit 50% colony formation of cells, expressed by $IC_{50}$, are calculated from the counted number of colonies. Further, there was determined an activity of overcoming the multidrug resistance, which is a relative value based on $IC_{50}$ value obtained for the control(administration of adriamycin alone) in Pharmacological Example 2. The results are shown in the following Table 3.

TABLE 3

Combined effect of present compounds and adriamycin on MCF 7/ADM

| Test compound | Combined concentration (µM) | ADM $IC_{50}$ (ng/ml) | Activity of overcoming multidrug resistance |
|---|---|---|---|
| (RUN 1) | | | |
| Control (ADM) in Pharmacological Example 2 | — | 10 | 1.0* |
| Control (ADM) in Pharmacological Example 3 | — | 1250 | 125** |
| Compound of Example 1 (dihydrochloride) | 50 | 30 | 3 |
| Compound of Example 6 (dihydrochloride) | 1 | 650 | 65 |
| (RUN 2) | | | |
| Control (ADM) in Pharmacological Example 2 | — | 3.6 | 1.0* |
| Control (ADM) in Pharmacological Example 3 | — | 750 | 208** |
| Compound of Example 4 (dihydrochloride) | 50 | 140 | 39 |
| Compound of Example 7 (dihydrochloride) | 20 | 190 | 53 |

Note:
*Activity obtained by single administration of adriamycin to adriamycin non-resistant cells (MCF 7/WT), which was conducted in Pharmacological Example 2.
**Activity obtained by single administration of adriamycin to adriamycin resistant cells (MCF 7/ADM).

The above results indicate that the compounds of the present invention have an activity of overcoming the multidrug resistance to adriamycin resistant cells derived from human breast cancer.

As evidenced by the above pharmacological tests, the compounds of formula (I) and its salts according to the invention have a low cytotoxicity, and enhance an activity of anti-cancer agents in non-resistant cancer cells, and also have an activity of overcoming resistance to multidrug resistant cancer cells.

Accordingly, the present compounds of formula (I) and its salts are useful as multidrug resistance inhibitors and agents for enhancing the activity of anti-cancer agents.

Pharmaceutical preparations comprising as an active ingredient the present compound or pharmaceutically

45 acceptable salts thereof are illustrated by the following pharmaceutical examples.

Pharmaceutical Example 1 Hard capsules

A mixture of 25 g of trans-N,N'-bis(3,4-dimethoxybenzyl)-N-solanesyl-1, 2-diaminocyclohexane (the compound of Example 1) and 7.5 g of polyoxyethylene castor oil was dissolved in methanol and mixed with 25 g of silicic anhydride. After methanol was evaporated off, the mixture was further incorporated with 5 g of calcium carboxymethylcellulose, 5 g of corn starch, 7.5 g of hydroxypropylcellulose and 20 g of microcrystalline cellulose, and further 30 ml of water. The mixture was kneaded and pelletized by means of a pelletizer equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 200 mg per capsule.

Pharmaceutical Example 2 Soft capsules

A homogeneous solution was prepared by mixing 30 g of trans-N,N'-bis(3,4-dimethoxybenzyl)-N-solanesyl-1,2-diaminocyclohexane (the compound of Example 1) with 130 g of polyethylene glycol (Macrogol 400). Separately, a gelatin solution was prepared which contained 93 g of gelatin, 19 g of glycerol, 10 g of D-sorbitol, 0.4 g of ethyl p-hydroxybenzoate, 0.2 g of propyl p-hydroxybenzoate and 0.4 g of titanium oxide. The gelatin solution was used as a capsule film forming agent. The previously obtained solution, together with the capsule film forming agent, was treated with a manual type flat punching machine to obtain capsules, each having the contents of 190 mg.

Pharmaceutical Example 3 Soft capsules

A homogeneous solution was prepared by mixing 40 g of trans-N,N'-bis(3,4-dimethoxybenzyl)-N-solanesyl-1,2-diaminocyclohexane (the compound of Example 1) with 120 g of polyethylene glycol (Macrogol 400). Separately, a gelatin solution was prepared which contained 90 g of gelatin, 16 g of glycerol, 8 g of D-sorbitol, 0.35 g of ethyl p-hydroxybenzoate, 0.2 g of propyl p-hydroxybenzoate and 0.3 g of titanium oxide. The gelatin solution was used as a capsule film forming agent. The previously obtained solution, together with the capsule film forming agent, was treated with a manual type flat punching machine to obtain capsules, each having the contents of 180 mg.

Pharmaceutical Example 4 Injections 5 g of trans-N,N'-bis(3,4-dimethoxybenzyl)-N-solanesyl-1, 2-diaminocyclohexane dihydrochloride, an appropriate amount of peanut oil and 1 g of benzyl alcohol were mixed, and further peanut oil was added to make up a total of 100 ml. This solution was dispensed in an amount of 1 ml under asepsis operation into an ampule which was then sealed.

Pharmaceutical Example 5 Injections 9 g of trans-N,N'-bis(3,4-dimethoxybenzyl)-N-solanesyl-1, 2-diaminocyclohexane dihydrochloride, 5.0 g of hydrogenated castor oil polyoxyetylene (60 mols) ether.

("Nikkol HCO 60", available from Nikko Chemical Co., Ltd.), 20 g of propylene glycol, 10 g of glycerol and 5.0 g of ethanol were mixed. To the mixture were added 100 ml of distilled water and stirred. Under asepsis operation, this solution was dispensed in an amount of 2 ml into an ampule which was then sealed.

What is claimed is:

1. An isoprene compound of formula (I)

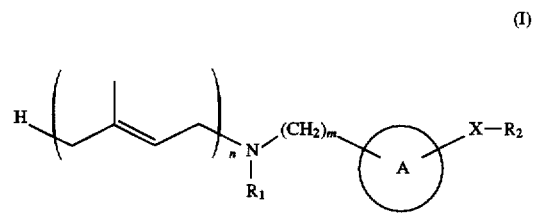

(I)

wherein m is an integer 0 to 3, n is an integer of 5 to 12,

A is cyclo($C_3$–$C_6$)alkylene, phenylene or fluorenylene, $R_1$ and $R_2$ are each independently benzyl, of which a phenyl ring may be substituted by 1 to 5 substituents selected from the group consisting of hydroxy, ($C_1$–$C_4$) alkyl, ($C_1$–$C_4$)alkoxy, and halogen, X is a single bond, or a divalent radical of —($CH_2$)$_p$ NH—, p is aninteger of 0 to 3, or a pharmaceutically acceptable salt thereof.

2. The isoprene compound of claim 1 wherein A is cyclo($C_3$–$C_6$)alkylene.

3. The isoprene compound of claim 1 wherein A is cyclohexylene.

4. A pharmaceutical composition which comprises as an active ingredient the isoprene compound claimed in claim 1 or a pharmaceutically acceptable salt thereof.

5. An agent for enhancing the activity of anti-cancer agents, comprising the isoprene compound as claimed in claim 1 or a pharmaceutically acceptable salt thereof, and a pharmaceutically acceptable carrier.

6. The agent of claim 5 wherein said anti-cancer agents are selected from the group consisting of anti-cancer agents effective for the treatment of brain tumor, kidney cancer, adrenal cancer, large intestine cancer, small intestine cancer, intestinum colon cancer, lung cancer, liver cancer, pancreas cancer and leukemia.

7. A process of preparing a compound of claim 1 which comprises reacting a compound of formula (II)

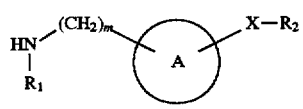

(II)

wherein m, A, X, $R_1$ and $R_2$ are as defined in claim 1, with a compound of formula (III)

(III)

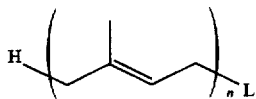

wherein n is as defined in claim 1, and L is a leaving group selected from the group consisting of halogen, $C_1$–$C_4$ alkylsulfonyloxy and arylsulfonyloxy.

8. The agent of claim 5, wherein the anti-cancer agent is taxol or taxotere.

9. A multidrug resistance inhibitor, comprising:
the isoprene compound as claimed in claim 1 or a pharmaceutically acceptable salt thereof; and
a pharmaceutically acceptable carrier.

10. The agent of claim 5, wherein said anti-cancer agents are selected from the group consisting of mitomycin, cyclophosphamide, melphalan, nimustine, carboquone, vincristine, vinblastine, vindesine, bleomycin, 5-fluorouracil, adriamycin, cisplatin, actinomycin D, methotrexate, aclarubicin, toyomycin, neocarzinostatin, ifosfamide, etoposide, camptothecin, doxorubicin and irinotecan.

* * * * *